US006153406A

United States Patent [19]
Tai et al.

[11] Patent Number: 6,153,406
[45] Date of Patent: Nov. 28, 2000

[54] **METHOD FOR THE HIGH LEVEL EXPRESSION, PURIFICATION AND REFOLDING OF THE OUTER MEMBRANE PROTEIN P2 FROM *HAEMOPHILUS INFLUENZAE* TYPE B**

[75] Inventors: Joseph Y. Tai, Fort Washington, Pa.; Jeffrey K. Pullen, Columbia; Thomas Soper, Laurel, both of Md.; Shu-Mei Liang, Taipei, Taiwan; Milan S. Blake, Fulton, Md.

[73] Assignee: North American Vaccine, Inc., Columbia, Md.

[21] Appl. No.: 08/096,181

[22] Filed: Jul. 23, 1993

(Under 37 CFR 1.47)

[51] Int. Cl.[7] ............................. C12N 15/09; C12N 1/20; C12P 21/04; A61K 39/102
[52] U.S. Cl. .................... 435/69.3; 424/256.1; 435/69.7; 435/252.8; 435/252.33; 435/172.3
[58] Field of Search ................................. 424/92, 256.1; 435/69.3, 69.7, 252.8, 252.33, 172.3

[56] References Cited

U.S. PATENT DOCUMENTS

| | | | |
|---|---|---|---|
| 4,356,170 | 10/1982 | Jennings et al. | 424/92 |
| 4,455,296 | 6/1984 | Hansen et al. | 424/87 |
| 4,459,286 | 7/1984 | Hilleman | 424/87 |
| 4,656,255 | 4/1987 | Seely | 530/412 |
| 4,695,624 | 9/1987 | Marburg et al. | 530/395 |
| 4,902,506 | 2/1990 | Anderson et al. | 424/92 |
| 5,173,294 | 12/1992 | Murphy et al. | 424/86 |
| 5,192,540 | 3/1993 | Kuo et al. | 424/92 |
| 5,196,338 | 3/1993 | Anilionis et al. | 435/252.3 |
| 5,503,992 | 4/1996 | Brodeur et al. | 435/69.3 |
| 5,576,002 | 11/1996 | Jennings et al. | 424/197.11 |
| 5,747,287 | 5/1998 | Blake et al. | 435/69.1 |
| 5,851,519 | 12/1998 | Dougan et al. | 424/93.2 |
| 5,858,677 | 1/1999 | Forsgren | 435/6 |
| 5,866,135 | 2/1999 | Blake et al. | 424/197.11 |
| 5,879,686 | 3/1999 | Blake et al. | 424/249.1 |
| 5,916,562 | 6/1999 | Munson, Jr. et al. | 424/190.1 |

FOREIGN PATENT DOCUMENTS

| | | |
|---|---|---|
| 0 320 289 A1 | 6/1989 | European Pat. Off. . |
| 0 378 929 A2 | 7/1990 | European Pat. Off. . |
| WO 90/06696 | 6/1990 | WIPO . |
| WO 92/01001 | 1/1992 | WIPO . |

OTHER PUBLICATIONS

Gibco BRL Catalogue & Reference Guide 1992 (Copyright 1991) see pp. 355 and 357.
Morston et al. Methods in Enzymology 182:264–276 1990.
Eisele et al, JBC, 265(18):10217–10220, Jun. 1990.
Blanco et al, J. Bacteriol, 178(23):6685–6692, Dec. 1996.
Champion et al J. Bacteriol, 179(4):1230–1238, Feb. 1997.
Srikumar et al, Infect&Imm. 61/8:3334–3341, Aug. 1993.
Dahan et al, FEBS Letters 392:304–308, 1996.
Skare et al, J. Bacteriol, 178/16:4909–4918, Aug. 1996.

Eisele, J.–L. and Rosenbusch, J.P., "In Vitro Folding and Oligomerization of a Membrane Protein," *J. Biol. Chem.* 265:10217–10220 (Jun. 1990).

Beuvery, E.C. et al., Preparation and Immunochemical Characterization of Meningococcal Group C Polysaccharide–Tetanus Toxoid Conjugates as a New Generation of Vaccines, *Infect. Immun.* 40:39–45 (Apr. 1983).

Blaseio, U. et al., Transformation of *Halobacterium halobium*: Development of vectors and investigation of gas vesicle synthesis, *Proc. Natl. Acad. Sci. USA* 87:6772–6776 (Sep. 1990).

Bremer, E. et al., Isolation and characterization of mutants deleted for the sulA–ompA region of the *Escherichia coli* K–12 chromosome, *FEMS Microbiol. Lett.* 33:173–178 (1986).

Cline, S.W. et al., Transformation of the Archaebacterium *Halobacterium volcanii* with Genomic DNA, *J. Bacteriol.* 171:4987–4991 (Sep. 1989).

Coleman, T. et al., Molecular Cloning, Expression, and Sequence of the Pilin Gene from Nontypeable *Haemophilus influenzae* M37, *Infect. Immun.* 59(5):1716–1722 (May 1991).

Duim, B. et al., Genetic Analysis of the Variability in Outer Membrane Protein P2 of Non–encapsulated *Haemophilus–influenzae*, *Abstract Gen. Meet. Am. Soc. Microbiol.* 92:88 Abstract No. B–374 (1992).

Forbes, K.J. et al., Variation in length and sequence of porin (ompP2) alleles of non–capsulate *Haemophilus influenzae*, *Molecular Microbiology* 6(15):2107–2112 (1992).

Hansen, E.J. et al., Cloning of the Gene Encoding the Major Outer Membrane Protein of *Haemophilus influenzae* Type b, *Infect. Immun.* 56:2709–2716 (Oct. 1988).

Hansen, E.J. et al., Primary Structure of the Porin Protein of *Haemophilus influenzae* Type b Determined by Nucleotide Sequence Analysis, *Infect. Immun.* 57:1100–1107 (Apr. 1989).

Jennings, H.J. et al., Immunochemistry of Groups A,B, and C Meningococcal Polysaccharide–Tetanus Toxoid Conjugates, *J. Immunol.* 127: 1011–1018 (Sep. 1981).

Jennings, H.J., Capsular Polysaccharides as Vaccine Candidates, *Current Topics in Microbiology and Immunology* 150:97–127 (1990).

(List continued on next page.)

*Primary Examiner*—Nita Minnifield
*Attorney, Agent, or Firm*—Sterne, Kessler, Goldstein & Fox, PLLC

[57] ABSTRACT

The present invention relates, in general, to a method of expressing the outer membrane protein P2 from *Haemophilus influenzae* type b (Hib-P2) and fusion proteins thereof. In particular, the present invention relates to a method of expressing the outer membrane protein P2 from *Haemophilus influenzae* type b or fusion protein thereof in *E. coli* wherein the Hib-P2 protein or fusion protein comprises more than 2% of the total protein expressed in *E. coli*. The invention also relates to a method of purification and refolding of Hib-P2 protein and fusion protein thereof.

41 Claims, 14 Drawing Sheets

OTHER PUBLICATIONS

Marburg, S. et al., Bimolecular Chemistry of Macromolecules: Synthesis of Bacterial Polysaccharide Conjugates with *Neisseria meningitidis* Membrane Protein, *J. Amer. Chem. Society* 108:5282–5287 (1986).

Martin, D. et al., Mapping of B–cell Epitopes on the Outer Membrane P2 Porin Protein of *Haemophilus influenzae* by Using Recombinant Proteins and Synthetic Peptides, *Infect. Immun.* 59(4):1457–1464 (Apr. 1991).

Munson, Jr., R. et al., Molecular Cloning, Expression, and Primary Sequence of Outer Membrane Protein P2 of *Haemophilus influenzae* Type b, *Infect. Immun.* 57:88–94 (Jan. 1989).

Munson, Jr., R.S. et al., Purification and Comparison of Outer Membrane Protein P2 from *Haemophilus influenzae* Type b Isolates, *J. Clin. Invest.* 72:677–684 (Aug. 1983).

Munson, Jr., R. et al., Purification, Cloning, and Sequence of Outer Membrane Protein P1 of *Haemophilus influenzae* Type b, *Infect. Immun.* 56(9):2235–2242 (Sep. 1988).

Munson, Jr., R. et al., Comparative Analysis of the Structures of the Outer Membrane Protein P1 Genes from Major Clones of *Haemophilus influenzae* Type b, *Infect. Immun.* 57(11):3300–3305 (Nov. 1989).

Munson, Jr., R. et al., Comparison of the Structure of the Genes for Outer Membrane Proteins P1 and P2 of *Haemophilus influenzae* Type b, *Molecular Immunology* 28(3):257–259 (1991).

Munson, Jr., R. et al., Diversity of the outer membrane protein P2 gene from major clones of *Haemophilus influenzae* type b, *Molecular Microbiology* 3(12):1797–1803 (1989).

Munson, Jr., R. et al., Outer Membrane Proteins P1 and P2 of *Haemophilus influenzae* Type b: Structure and Identification of Surface–Exposed Epitopes, *J. Infect. Dis.* 165(Suppl. 1):S86–S89 (1992).

Novagen Technical Bulletin: Plasmid map of pET–11a.

Robbins, J.B. et al., Polysaccharide–Protein Conjugates: A New Generation of Vaccines, *J. Infect. Dis.* 161:821–832 (1990).

Sanders, J.D. et al., Molecular Cloning of the Gene Encoding the P2 Protein of Nontypeable *Haemophilus–influenzae* (NTHI), *Abstract Gen. Meet. Am. Soc. Microbiol.* 92:87 Abstract No. B–371 (1992).

Schneerson, R. et al., Preparation, Characterization, and Immunogenicity of *Haemophilus influenzae* Type b Polysaccharide–Protein Conjugates, *J. Exp. Med.* 152:361–376 (1980).

Schneerson, R. et al., Quantitative and Qualitative Analyses of Serum Antibodies Elicited in Adults by *Haemophilus influenzae* Type b and Pneumococcus Type 6A Capsular Polysaccharide–Tetanus Toxoid Conjugates, *Infect. Immun.* 52:519–528 (May 1986).

Siber, G.R. et al., Preparation of Human Hyperimmune Globulin to *Haemophilus infleunzea* b, *Streptococcus pneumoniae,* and *Neisseria meningitidis, Infect. Immun.* 45:248–254 (Jul. 1984).

Sikkema, D.J. et al., Molecular Analysis of the P2 Genes of Nontypeable *Haemophilus influenzae, Abstract Gen. Meet. Am. Soc. Microbiol.* 92:88 Abstract No. B–372 (1992).

Sreekrishna et al., High level expression of heterologous proteins in methylotrophic yeast *Pichia pastoris, J. Basic Microbiol.* 28:265–278 (1988).

Studier, F.W. et al., Use of T7 RNA Polymerase to Direct Expression of Cloned Genes, *Methods in Enzymology* 185:60–89 (1990).

Tarkowski, A. et al., Immunization of Humans With Polysaccharide Vaccines Induces Systemic, Predominantly Polymeric IgA2–Subclass Antibody Responses, *J. Immunol.* 144:3770–3778 (May 15, 1990).

Vachon, V. et al., Transmembrane Permeability Channels across the Outer Membrane of *Haemophilus influenzae* Type b, *J. Bacteriol.* 162:918–924 (Jun. 1985).

Hirel, Ph.–H. et al., "Extent of N–terminal methionine excision from *Escherichia coli* proteins is governed by the side–chain length of the penultimate amino acid," *Proc. Natl. Acad. Sci. USA* 86(21):8247–8251 (1989).

Idänpään–Heikkilä, I. et al, "Immunization with meningococcal class 1 outer membrane protein produced in *Bacillus subtilis* and reconstituted in the presence of Zwittergent or Triton X–100," *Vaccine* 14:886–891 (Jun. 1996).

Muttilainen, S. et al., "Heterologous production of the P1 porin of *Neisseria meningitidis* in *Bacillus subtilis*: the effect of an N–terminal extension on the presentation of native–like epitopes," *Microb. Pathogen.* 18:365–371 (May 1995).

Muttilainen, S. et al., "The *Neisseria meningitidis* outer membrane protein P1 produced in *Bacillus subtilis* and reconstituted into phospholipid vesicles elicits antibodies to native P1 epitopes," *Microb. Pathogen.* 18:423–436 (May 1995).

Nurminen, M. et al. "The class 1 outer membrane protein of *Neisseria meningitidis* produced in *Bacillus subtilis* can give rise to protective immunity," *Mol. Microbiol.* 6:2499–2506 (Sep. 1992).

Qi, H.L. et al., "Expression of Large Amounts of Neisserial Porin Proteins in *Escherichia coli* and Refolding of the Proteins into Native Trimers," *Infect. Immun.* 62:2432–2439 (Jun. 1994).

Schmid, B. et al., "Expression of porin from *Rhodopseudomonas blastica* in *Escherichia coli* inclusion bodies and folding into exact native structure," *FEBS Lett.* 381:111–114 (Feb. 1996).

von Heijne, G., "A new method for predicting signal sequence cleavage sites," *Nucl. Acids Res.* 14:4683–4690 (Jun. 1986).

1 2 3 4 5 6 7 8 9 10 11 12 13 14

1 2 3 4 5 6 7 8 9 10 11 12 13 14

```
        SalI                        — oligo #1 —
        GTCGACAATT CTATTGGAGA AAAGTTCAAT CATAGATAGT AAACAACCAT AAGGAATACA        60

AseI
        AATT ATG AAA AAA ACA CTT GCA GCA TTA ATC GTT GGT GCA TTC GCA GCT        109
             Met Lys Lys Thr Leu Ala Ala Leu Ile Val Gly Ala Phe Ala Ala
              1           5                  10                  15

PvuII    — oligo #2 —
        TCA GCA GCA AAC GCA GCT GTT GTT TAT AAC AAC GAA GGG ACT AAC GTA        157
        Ser Ala Ala Asn Ala Ala Val Val Tyr Asn Asn Glu Gly Thr Asn Val
                          20              25                  30

— oligo #5 —
        GAA TTA GGT GGT CGT TTA AGC ATT ATC GCA GAA CAA AGT AAT AGC ACT        205
        Glu Leu Gly Gly Arg Leu Ser Ile Ile Ala Glu Gln Ser Asn Ser Thr
                      35              40                  45

— oligo #12 —
        GTA GAT AAT CAA AAA CAG CAA CAC GGT GCA TTA CGC AAT CAA GGT TCA        253
        Val Asp Asn Gln Lys Gln Gln His Gly Ala Leu Arg Asn Gln Gly Ser
                  50              55                  60

— oligo #13 —
        CGT TTC CAC ATT AAA GCA ACT CAT AAC TTC GGT GAT GGT TTC TAT GCA        301
        Arg Phe His Ile Lys Ala Thr His Asn Phe Gly Asp Gly Phe Tyr Ala
                  65              70                  75

CAA GGT TAT TTA GAA ACT CGT TTT GTT ACA AAA GCC TCT GAA AAC GGT        349
        Gln Gly Tyr Leu Glu Thr Arg Phe Val Thr Lys Ala Ser Glu Asn Gly
         80              85                  90                  95

TCA GAT AAC TTC GGT GAT ATT ACA AGC AAA TAT GCT TAT GTT ACT TTA        397
        Ser Asp Asn Phe Gly Asp Ile Thr Ser Lys Tyr Ala Tyr Val Thr Leu
                      100                 105                 110

— oligo #6 —
        GGA AAT AAA GCA TTC GGT GAA GTA AAA CTT GGT CGT GCG AAA ACT ATT        445
        Gly Asn Lys Ala Phe Gly Glu Val Lys Leu Gly Arg Ala Lys Thr Ile
                      115                 120                 125
```

FIG.4A

```
                    ─oligo #7─
     GCT GAT GGC ATA ACA AGT GCA GAA GAT AAA GAA TAT GGC GTT CTC AAC      493
     Ala Asp Gly Ile Thr Ser Ala Glu Asp Lys Glu Tyr Gly Val Leu Asn
             130             135             140

SpeI                            DraI
     AAT AGT GAC TAT ATT CCT ACT AGT GGT AAT ACG GTT GGC TAT ACT TTT      541
     Asn Ser Asp Tyr Ile Pro Thr Ser Gly Asn Thr Val Gly Tyr Thr Phe
             145             150             155

HhaI
     AAA GGT ATT GAT GGT TTA GTA TTA GGC GCT AAT TAT TTA TTA GCA CAA      589
     Lys Gly Ile Asp Gly Leu Val Leu Gly Ala Asn Tyr Leu Leu Ala Gln
     160             165             170             175

─oligo #8─                  FnuDI
     AAG CGT GAG GGT GCA AAA GGT GAA AAT AAG CGG CCT AAT GAT AAG GCT      637
     Lys Arg Glu Gly Ala Lys Gly Glu Asn Lys Arg Pro Asn Asp Lys Ala
                     180             185             190

SnaBI                        EcoRI
     GGT GAA GTA CGT ATA GGT GAA ATC AAT AAT GGA ATT CAA GTT GGT GCA      685
     Gly Glu Val Arg Ile Gly Glu Ile Asn Asn Gly Ile Gln Val Gly Ala
                     195             200             205

AAA TAT GAT GCA AAC GAC ATC GTT GCA AAA ATT GCT TAT GGT AGA ACT      733
     Lys Tyr Asp Ala Asn Asp Ile Val Ala Lys Ile Ala Tyr Gly Arg Thr
             210             215             220

─oligo #11─
     AAC TAC AAA TAT AAC GAA TCT GAC GAG CAT AAA CAG CAA TTA AAT GGT      781
     Asn Tyr Lys Tyr Asn Glu Ser Asp Glu His Lys Gln Gln Leu Asn Gly
             225             230             235

GTA TTA GCA ACT TTA GGC TAT CGT TTT AGT GAT TTA GGC TTA TTA GTG      829
     Val Leu Ala Thr Leu Gly Tyr Arg Phe Ser Asp Leu Gly Leu Leu Val
     240             245             250             255

XbaI        ─oligo #3─                              ─oligo #14─
     TCT CTA GAT AGT GGC TAT GCA AAA ACT AAA AAC TAT AAA ATT AAA CAC      877
     Ser Leu Asp Ser Gly Tyr Ala Lys Thr Lys Asn Tyr Lys Ile Lys His
                     260             265             270
```

FIG.4B

```
                                                             AseI
GAA AAA CGC TAT TTC GTA TCT CCA GGT TTC CAA TAT GAA TTA ATG GAA    925
Glu Lys Arg Tyr Phe Val Ser Pro Gly Phe Gln Tyr Glu Leu Met Glu
            275                 280                 285

GAT ACT AAT GTC TAT GGC AAC TTC AAA TAT GAA CGC ACT TCT GTA GAT    973
Asp Thr Asn Val Tyr Gly Asn Phe Lys Tyr Glu Arg Thr Ser Val Asp
            290                 295                 300

— oligo #16 —         — oligo #9 — Sau3A
CAA GGT GAA AAA ACA CGT GAA CAA GCA GTA TTA TTC GGT GTA GAT CAT    1021
Gln Gly Glu Lys Thr Arg Glu Gln Ala Val Leu Phe Gly Val Asp His
            305                 310                 315

AAA CTT CAC AAA CAA CTA TTA ACC TAT ATT GAA GGT GCT TAC GCT AGA    1069
Lys Leu His Lys Gln Leu Leu Thr Tyr Ile Glu Gly Ala Tyr Ala Arg
320                 325                 330                 335

ACT AGA ACA ACT GAG ACA GGT AAA GGC GTA AAA ACT GAA AAA GAA AAA    1117
Thr Arg Thr Thr Glu Thr Gly Lys Gly Val Lys Thr Glu Lys Glu Lys
            340                 345                 350

— oligo #15 —   MluI
TCA GTG GGT GTA GGT TTA CGC GTT TAC TTC TAATCATTTG TTAGAAATAC      1167
Ser Val Gly Val Gly Leu Arg Val Tyr Phe
            355                 360
                                              — oligo #4 —
ATTATTAAAA GCAAGGCGAA TCGAAAGATT CGCTTTTTTT GCTCAAAATC AAGTTAAAAA  1227

AseI
ATGATTAAGT TAAAAGTGTA TAAATATTTA GGCTATTTTA TAAGTAACAA AATATTAATA  1287

— PCR-4 —                DraI
AAAAATCTGT GACATATATC ACAGATTTTT AAATCAATTA ACTATTTAAG TGTTTACTAT  1347

AseI                                         PCR-5 —
TAATTCTCTT TCCACTTTCC GTTACTACT GTGCCGATTA CTTGGTAATT TGGCGTAAAC   1407

Sau3A
ACGGCTAAGT TGCTATCTT ACCTTTTCT ACCGAACCTA AACGATCATC TATACCAATT    1467

SalI                   FIG.4C
GCTCGTCGAC                                                         1477
```

```
         NdeI  NheI                                                    HindIII
    CAT  ATG  GCT  AGC  ATG  ACT  GGT  GGA  CAG  CAA  ATG  GGT  CGG  GAT  TCA  AGC        48
         Met  Ala  Ser  Met  Thr  Gly  Gly  Gln  Gln  Met  Gly  Arg  Asp  Ser  Ser
          1              5                        10                       15

KpnI           BamHI
    TTG  GTA  CCG  AGC  TCG  GAT  CCA  GCT  GTT  GTT  TAT  AAC  AAC  GAA  GGG  ACT        96
    Leu  Val  Pro  Ser  Ser  Asp  Pro  Ala  Val  Val  Tyr  Asn  Asn  Glu  Gly  Thr
                        20                   25                       30

AAC  GTA  GAA  TTA  GGT  GGT  CGT  TTA  AGC  ATT  ATC  GCA  GAA  CAA  AGT  AAT       144
    Asn  Val  Glu  Leu  Gly  Gly  Arg  Leu  Ser  Ile  Ile  Ala  Glu  Gln  Ser  Asn
                        35                   40                       45

AGC  ACT  GTA  GAT  AAT  CAA  AAA  CAG  CAA  CAC  GGT  GCA  TTA  CGC  AAT  CAA       192
    Ser  Thr  Val  Asp  Asn  Gln  Lys  Gln  Gln  His  Gly  Ala  Leu  Arg  Asn  Gln
                        50                   55                       60

GGT  TCA  CGT  TTC  CAC  ATT  AAA  GCA  ACT  CAT  AAC  TTC  GGT  GAT  GGT  TTC       240
    Gly  Ser  Arg  Phe  His  Ile  Lys  Ala  Thr  His  Asn  Phe  Gly  Asp  Gly  Phe
         65                   70                       75

TAT  GCA  CAA  GGT  TAT  TTA  GAA  ACT  CGT  TTT  GTT  ACA  AAA  GCC  TCT  GAA       288
    Tyr  Ala  Gln  Gly  Tyr  Leu  Glu  Thr  Arg  Phe  Val  Thr  Lys  Ala  Ser  Glu
    80                   85                       90                       95

AAC  GGT  TCA  GAT  AAC  TTC  GGT  GAT  ATT  ACA  AGC  AAA  TAT  GCT  TAT  GTT       336
    Asn  Gly  Ser  Asp  Asn  Phe  Gly  Asp  Ile  Thr  Ser  Lys  Tyr  Ala  Tyr  Val
                       100                  105                      110

ACT  TTA  GGA  AAT  AAA  GCA  TTC  GGT  GAA  GTA  AAA  CTT  GGT  CGT  GCG  AAA       384
    Thr  Leu  Gly  Asn  Lys  Ala  Phe  Gly  Glu  Val  Lys  Leu  Gly  Arg  Ala  Lys
                       115                  120                      125

ACT  ATT  GCT  GAT  GGC  ATA  ACA  AGT  GCA  GAA  GAT  AAA  GAA  TAT  GGC  GTT       432
    Thr  Ile  Ala  Asp  Gly  Ile  Thr  Ser  Ala  Glu  Asp  Lys  Glu  Tyr  Gly  Val
                       130                  135                      140
```

FIG.5A

```
                                              SpeI
CTC AAC AAT AGT GAC TAT ATT CCT ACT AGT GGT AAT ACG GTT GGC TAT       480
Leu Asn Asn Ser Asp Tyr Ile Pro Thr Ser Gly Asn Thr Val Gly Tyr
        145                 150                 155

DraI                                        HhaI
ACT TTT AAA GGT ATT GAT GGT TTA GTA TTA GGC GCT AAT TAT TTA TTA       528
Thr Phe Lys Gly Ile Asp Gly Leu Val Leu Gly Ala Asn Tyr Leu Leu
160             165                 170                 175

FnuDI
GCA CAA AAG CGT GAG GGT GCA AAA GGT GAA AAT AAG CGG CCT AAT GAT       576
Ala Gln Lys Arg Glu Gly Ala Lys Gly Glu Asn Lys Arg Pro Asn Asp
                180                 185                 190

SnaBI                           EcoRI
AAG GCT GGT GAA GTA CGT ATA GGT GAA ATC AAT AAT GGA ATT CAA GTT       624
Lys Ala Gly Glu Val Arg Ile Gly Glu Ile Asn Asn Gly Ile Gln Val
            195                 200                 205

GGT GCA AAA TAT GAT GCA AAC GAC ATC GTT GCA AAA ATT GCT TAT GGT       672
Gly Ala Lys Tyr Asp Ala Asn Asp Ile Val Ala Lys Ile Ala Tyr Gly
            210                 215                 220

AGA ACT AAC TAC AAA TAT AAC GAA TCT GAC GAG CAT AAA CAG CAA TTA       720
Arg Thr Asn Tyr Lys Tyr Asn Glu Ser Asp Glu His Lys Gln Gln Leu
        225                 230                 235

AAT GGT GTA TTA GCA ACT TTA GGC TAT CGT TTT AGT GAT TTA GGC TTA       768
Asn Gly Val Leu Ala Thr Leu Gly Tyr Arg Phe Ser Asp Leu Gly Leu
240             245                 250                 255

XbaI
TTA GTG TCT CTA GAT AGT GGC TAT GCA AAA ACT AAA AAC TAT AAA ATT       816
Leu Val Ser Leu Asp Ser Gly Tyr Ala Lys Thr Lys Asn Tyr Lys Ile
                260                 265                 270

AseI
AAA CAC GAA AAA CGC TAT TTC GTA TCT CCA GGT TTC CAA TAT GAA TTA       864
Lys His Glu Lys Arg Tyr Phe Val Ser Pro Gly Phe Gln Tyr Glu Leu
            275                 280                 285
```

FIG.5B

```
ATG GAA GAT ACT AAT GTC TAT GGC AAC TTC AAA TAT GAA CGC ACT TCT        912
Met Glu Asp Thr Asn Val Tyr Gly Asn Phe Lys Tyr Glu Arg Thr Ser
        290                 295                 300

GTA GAT CAA GGT GAA AAA ACA CGT GAA CAA GCA GTA TTA TTC GGT GTA        960
Val Asp Gln Gly Glu Lys Thr Arg Glu Gln Ala Val Leu Phe Gly Val
        305                 310                 315

GAT CAT AAA CTT CAC AAA CAA CTA TTA ACC TAT ATT GAA GGT GCT TAC       1008
Asp His Lys Leu His Lys Gln Leu Leu Thr Tyr Ile Glu Gly Ala Tyr
320                 325                 330                 335

GCT AGA ACT AGA ACA ACT GAG ACA GGT AAA GGC GTA AAA ACT GAA AAA       1056
Ala Arg Thr Arg Thr Thr Glu Thr Gly Lys Gly Val Lys Thr Glu Lys
                340                 345                 350

MluI
GAA AAA TCA GTG GGT GTA GGT TTA CGC GTT TAC TTC TAATCATTTG            1102
Glu Lys Ser Val Gly Val Gly Leu Arg Val Tyr Phe
                355                 360

XhoI
TTAGAAATAC ATTATTAAAA GCAAGGCGAC TCGAG ......                         1137
```

FIG.5C

```
         NdeI
     CAT ATG GCT GTT GTT TAT AAC AAC GAA GGG ACT AAC GTA GAA TTA GGT         48
         Met Ala Val Val Tyr Asn Asn Glu Gly Thr Asn Val Glu Leu Gly
          1               5                  10                  15

GGT CGT TTA AGC ATT ATC GCA GAA CAA AGT AAT AGC ACT GTA GAT AAT         96
     Gly Arg Leu Ser Ile Ile Ala Glu Gln Ser Asn Ser Thr Val Asp Asn
                      20                  25                  30

CAA AAA CAG CAA CAC GGT GCA TTA CGC AAT CAA GGT TCA CGT TTC CAC        144
     Gln Lys Gln Gln His Gly Ala Leu Arg Asn Gln Gly Ser Arg Phe His
                  35                  40                  45

ATT AAA GCA ACT CAT AAC TTC GGT GAT GGT TTC TAT GCA CAA GGT TAT        192
     Ile Lys Ala Thr His Asn Phe Gly Asp Gly Phe Tyr Ala Gln Gly Tyr
              50                  55                  60

TTA GAA ACT CGT TTT GTT ACA AAA GCC TCT GAA AAC GGT TCA GAT AAC        240
     Leu Glu Thr Arg Phe Val Thr Lys Ala Ser Glu Asn Gly Ser Asp Asn
          65                  70                  75

TTC GGT GAT ATT ACA AGC AAA TAT GCT TAT GTT ACT TTA GGA AAT AAA        288
     Phe Gly Asp Ile Thr Ser Lys Tyr Ala Tyr Val Thr Leu Gly Asn Lys
      80                  85                  90                  95

GCA TTC GGT GAA GTA AAA CTT GGT CGT GCG AAA ACT ATT GCT GAT GGC        336
     Ala Phe Gly Glu Val Lys Leu Gly Arg Ala Lys Thr Ile Ala Asp Gly
                     100                 105                 110

ATA ACA AGT GCA GAA GAT AAA GAA TAT GGC GTT CTC AAC AAT AGT GAC        384
     Ile Thr Ser Ala Glu Asp Lys Glu Tyr Gly Val Leu Asn Asn Ser Asp
                 115                 120                 125

SpeI                            DraI
     TAT ATT CCT ACT AGT GGT AAT ACG GTT GGC TAT ACT TTT AAA GGT ATT        432
     Tyr Ile Pro Thr Ser Gly Asn Thr Val Gly Tyr Thr Phe Lys Gly Ile
             130                 135                 140

HhaI
     GAT GGT TTA GTA TTA GGC GCT AAT TAT TTA TTA GCA CAA AAG CGT GAG        480
     Asp Gly Leu Val Leu Gly Ala Asn Tyr Leu Leu Ala Gln Lys Arg Glu
         145                 150                 155
```

FIG. 6A

| | |
|---|---|
| GGT GCA AAA GGT GAA AAT AAG CGG CCT AAT GAT AAG GCT GGT GAA GTA<br>Gly Ala Lys Gly Glu Asn Lys Arg Pro Asn Asp Lys Ala Gly Glu Val<br>160               165             170             175 | 528 |
|                                   EcoRI<br>CGT ATA GGT GAA ATC AAT AAT GGA ATT CAA GTT GGT GCA AAA TAT GAT<br>Arg Ile Gly Glu Ile Asn Asn Gly Ile Gln Val Gly Ala Lys Tyr Asp<br>             180                 185               190 | 576 |
| GCA AAC GAC ATC GTT GCA AAA ATT GCT TAT GGT AGA ACT AAC TAC AAA<br>Ala Asn Asp Ile Val Ala Lys Ile Ala Tyr Gly Arg Thr Asn Tyr Lys<br>             195                 200               205 | 624 |
| TAT AAC GAA TCT GAC GAG CAT AAA CAG CAA TTA AAT GGT GTA TTA GCA<br>Tyr Asn Glu Ser Asp Glu His Lys Gln Gln Leu Asn Gly Val Leu Ala<br>             210                 215               220 | 672 |
|                                                   XbaI<br>ACT TTA GGC TAT CGT TTT AGT GAT TTA GGC TTA TTA GTG TCT CTA GAT<br>Thr Leu Gly Tyr Arg Phe Ser Asp Leu Gly Leu Leu Val Ser Leu Asp<br>225               230                 235 | 720 |
| AGT GGC TAT GCA AAA ACT AAA AAC TAT AAA ATT AAA CAC GAA AAA CGC<br>Ser Gly Tyr Ala Lys Thr Lys Asn Tyr Lys Ile Lys His Glu Lys Arg<br>240               245                 250             255 | 768 |
|                                   AseI<br>TAT TTC GTA TCT CCA GGT TTC CAA TAT GAA TTA ATG GAA GAT ACT AAT<br>Tyr Phe Val Ser Pro Gly Phe Gln Tyr Glu Leu Met Glu Asp Thr Asn<br>             260                 265               270 | 816 |
| GTC TAT GGC AAC TTC AAA TAT GAA CGC ACT TCT GTA GAT CAA GGT GAA<br>Val Tyr Gly Asn Phe Lys Tyr Glu Arg Thr Ser Val Asp Gln Gly Glu<br>             275                 280               285 | 864 |
| AAA ACA CGT GAA CAA GCA GTA TTA TTC GGT GTA GAT CAT AAA CTT CAC<br>Lys Thr Arg Glu Gln Ala Val Leu Phe Gly Val Asp His Lys Leu His<br>             290                 295               300 | 912 |
| AAA CAA CTA TTA ACC TAT ATT GAA GGT GCT TAC GCT AGA ACT AGA ACA<br>Lys Gln Leu Leu Thr Tyr Ile Glu Gly Ala Tyr Ala Arg Thr Arg Thr<br>305               310                 315 | 960 |

FIG. 6B

```
ACT GAG ACA GGT AAA GGC GTA AAA ACT GAA AAA GAA AAA TCA GTG GGT        1008
Thr Glu Thr Gly Lys Gly Val Lys Thr Glu Lys Glu Lys Ser Val Gly
320             325             330             335

MluI
GTA GGT TTA CGC GTT TAC TTC TAATCATTTG TTAGAAATAC ATTATTAAAA            1059
Val Gly Leu Arg Val Tyr Phe end
                340

XhoI
GCAAGGCGAC TCGAG ......                                                 1074
```

FIG. 6C

```
       NdeI
CAT ATG GCT GTT GTT TAT AAC AAC GAA GGG ACT AAC GTA GAA TTA GGT      48
    Met Ala Val Val Tyr Asn Asn Glu Gly Thr Asn Val Glu Leu Gly
     1           5                  10                  15

GGT CGT TTA AGC ATT ATC GCA GAA CAA AGT AAT AGC ACT GTA GAT AAT      96
Gly Arg Leu Ser Ile Ile Ala Glu Gln Ser Asn Ser Thr Val Asp Asn
                 20                  25                  30

CAA AAA CAG CAA CAC GGT GCA TTA CGC AAT CAA GGT TCA CGT TTC CAC     144
Gln Lys Gln Gln His Gly Ala Leu Arg Asn Gln Gly Ser Arg Phe His
             35                  40                  45

ATT AAA GCA ACT CAT AAC TTC GGT GAT GGT TTC TAT GCA CAA GGT TAT     192
Ile Lys Ala Thr His Asn Phe Gly Asp Gly Phe Tyr Ala Gln Gly Tyr
         50                  55                  60

TTA GAA ACT CGT TTT GTT ACA AAA GCC TCT GAA AAC GGT TCA GAT AAC     240
Leu Glu Thr Arg Phe Val Thr Lys Ala Ser Glu Asn Gly Ser Asp Asn
     65                  70                  75

TTC GGT GAT ATT ACA AGC AAA TAT GCT TAT GTT ACT TTA GGA AAT AAA     288
Phe Gly Asp Ile Thr Ser Lys Tyr Ala Tyr Val Thr Leu Gly Asn Lys
 80                  85                  90                  95

GCA TTC GGT GAA GTA AAA CTT GGT CGT GCG AAA ACT ATT GCT GAT GGC     336
Ala Phe Gly Glu Val Lys Leu Gly Arg Ala Lys Thr Ile Ala Asp Gly
                100                 105                 110

ATA ACA AGT GCA GAA GAT AAA GAA TAT GGC GTT CTC AAC AAT AGT GAC     384
Ile Thr Ser Ala Glu Asp Lys Glu Tyr Gly Val Leu Asn Asn Ser Asp
             115                 120                 125

SpeI                             DraI
TAT ATT CCT ACT AGT GGT AAT ACC GTT GGC TAT ACT TTT AAA GGT ATT     432
Tyr Ile Pro Thr Ser Gly Asn Thr Val Gly Tyr Thr Phe Lys Gly Ile
         130                 135                 140

HhaI
GAT GGT TTA GTA TTA GGC GCT AAT TAT TTA TTA GCA CAA AAG CGT GAG     480
Asp Gly Leu Val Leu Gly Ala Asn Tyr Leu Leu Ala Gln Lys Arg Glu
         145                 150                 155
```

FIG. 7A

```
GGT GCA AAA GGT GAA AAT AAG CGG CCT AAT GAT AAG GCT GGT GAA GTA          528
Gly Ala Lys Gly Glu Asn Lys Arg Pro Asn Asp Lys Ala Gly Glu Val
160             165             170             175

EcoRI
CGT ATA GGT GAA ATC AAT AAT GGA ATT CAA GTT GGT GCA AAA TAT GAT          576
Arg Ile Gly Glu Ile Asn Asn Gly Ile Gln Val Gly Ala Lys Tyr Asp
            180             185             190

GCA AAC GAC ATC GTT GCA AAA ATT GCT TAT GGT AGA ACT AAC TAC AAA          624
Ala Asn Asp Ile Val Ala Lys Ile Ala Tyr Gly Arg Thr Asn Tyr Lys
            195             200             205

TAT AAC GAA TCT GAC GAG CAT AAA CAG CAA TTA AAT GGT GTA TTA GCA          672
Tyr Asn Glu Ser Asp Glu His Lys Gln Gln Leu Asn Gly Val Leu Ala
        210             215             220
                                                        XbaI
ACT TTA GGC TAT CGT TTT AGT GAT TTA GGC TTA TTA GTG TCT CTA GAT          720
Thr Leu Gly Tyr Arg Phe Ser Asp Leu Gly Leu Leu Val Ser Leu Asp
    225             230             235

AGT GGC TAT GCA AAA ACT AAA AAC TAT AAA ATT AAA CAC GAA AAA CGC          768
Ser Gly Tyr Ala Lys Thr Lys Asn Tyr Lys Ile Lys His Glu Lys Arg
240             245             250             255

AseI
TAT TTC GTA TCT CCA GGT TTC CAA TAT GAA TTA ATG GAA GAT ACT AAT          816
Tyr Phe Val Ser Pro Gly Phe Gln Tyr Glu Leu Met Glu Asp Thr Asn
            260             265             270

GTC TAT GGC AAC TTC AAA TAT GAA CGC ACT TCT GTA GAT CAA GGT GAA          864
Val Tyr Gly Asn Phe Lys Tyr Glu Arg Thr Ser Val Asp Gln Gly Glu
            275             280             285

AAA ACA CGT GAA CAA GCA GTA TTA TTC GGT GTA GAT CAT AAA CTT CAC          912
Lys Thr Arg Glu Gln Ala Val Leu Phe Gly Val Asp His Lys Leu His
        290             295             300
```

FIG. 7B

```
                    290                     295                          300
AAA CAA CTA TTA ACC TAT ATT GAA GGT GCT TAC GCT AGA ACT AGA ACA              960
Lys Gln Leu Leu Thr Tyr Ile Glu Gly Ala Tyr Ala Arg Thr Arg Thr
    305                     310                         315

ACT GAG ACA GGT AAA GGC GTA AAA ACT GAA AAA GAA AAA TCA GTG GGT              1008
Thr Glu Thr Gly Lys Gly Val Lys Thr Glu Lys Glu Lys Ser Val Gly
320                     325                         330                  335

MluI
GTA GGT TTA CGC GTT TAC TTC TAATCATTTG TTAGAAATAC ATTATTAAAA                 1059
Val Gly Leu Arg Val Tyr Phe
                    340
        BamHI
GCAAGGCGGA TCC . . . . . .                                                   1072
```

FIG. 7C

```
                          SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:1:

TTCTGGCGAG TCGACAATTC TATTGG                                            26

(2) INFORMATION FOR SEQ ID NO:2:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:2:

AACCTTTATC GTCGACGAGC AATTGG                                            26

(2) INFORMATION FOR SEQ ID NO:3:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (xi) SEQUENCE DESCRIPTION: SEQ ID NO:3:

GCTTCAGCAG CACATATGGC TGTTGTTTAT AACAACGAAG GGAC                         44

(2) INFORMATION FOR SEQ ID NO:4:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (xi) SEQUENCE DESCRIPTION: SEQ ID NO:4:

GCAGCTTCAG CAGCGGATCC AGCTGTTGTT TATAACAACG AAGGG                        45

(2) INFORMATION FOR SEQ ID NO:5:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (xi) SEQUENCE DESCRIPTION: SEQ ID NO:5:
```

-continued

```
GCAAAAAAAG CGAATCTCTC GAGTCGCCTT GCTTT                                35
```

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:6:

```
AAAAAAAGCG AATCTTTGGA TCCGCCTTGC TTTTAATAAT G                          41
```

(2) INFORMATION FOR SEQ ID NO:7:

(i) SEQUENCE CHARACTERISTICS:
        (A) LENGTH: 1477 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 65..1147

(xi) SEQUENCE DESCRIPTION: SEQ ID NO:7:

```
GTCGACAATT CTATTGGAGA AAAGTTCAAT CATAGATAGT AAACAACCAT AAGGAATACA      60

AATT ATG AAA AAA ACA CTT GCA GCA TTA ATC GTT GGT GCA TTC GCA GCT     109
     Met Lys Lys Thr Leu Ala Ala Leu Ile Val Gly Ala Phe Ala Ala
     1               5                  10                  15

TCA GCA GCA AAC GCA GCT GTT GTT TAT AAC AAC GAA GGG ACT AAC GTA     157
Ser Ala Ala Asn Ala Ala Val Val Tyr Asn Asn Glu Gly Thr Asn Val
                20                  25                  30

GAA TTA GGT GGT CGT TTA AGC ATT ATC GCA GAA CAA AGT AAT AGC ACT     205
Glu Leu Gly Gly Arg Leu Ser Ile Ile Ala Glu Gln Ser Asn Ser Thr
            35                  40                  45

GTA GAT AAT CAA AAA CAG CAA CAC GGT GCA TTA CGC AAT CAA GGT TCA     253
Val Asp Asn Gln Lys Gln Gln His Gly Ala Leu Arg Asn Gln Gly Ser
        50                  55                  60

CGT TTC CAC ATT AAA GCA ACT CAT AAC TTC GGT GAT GGT TTC TAT GCA     301
Arg Phe His Ile Lys Ala Thr His Asn Phe Gly Asp Gly Phe Tyr Ala
    65                  70                  75

CAA GGT TAT TTA GAA ACT CGT TTT GTT ACA AAA GCC TCT GAA AAC GGT     349
Gln Gly Tyr Leu Glu Thr Arg Phe Val Thr Lys Ala Ser Glu Asn Gly
80                  85                  90                  95

TCA GAT AAC TTC GGT GAT ATT ACA AGC AAA TAT GCT TAT GTT ACT TTA     397
Ser Asp Asn Phe Gly Asp Ile Thr Ser Lys Tyr Ala Tyr Val Thr Leu
                100                 105                 110

GGA AAT AAA GCA TTC GGT GAA GTA AAA CTT GGT CGT GCG AAA ACT ATT     445
Gly Asn Lys Ala Phe Gly Glu Val Lys Leu Gly Arg Ala Lys Thr Ile
            115                 120                 125

GCT GAT GGC ATA ACA AGT GCA GAA GAT AAA GAA TAT GGC GTT CTC AAC     493
Ala Asp Gly Ile Thr Ser Ala Glu Asp Lys Glu Tyr Gly Val Leu Asn
        130                 135                 140

AAT AGT GAC TAT ATT CCT ACT AGT GGT AAT ACG GTT GGC TAT ACT TTT     541
Asn Ser Asp Tyr Ile Pro Thr Ser Gly Asn Thr Val Gly Tyr Thr Phe
    145                 150                 155

AAA GGT ATT GAT GGT TTA GTA TTA GGC GCT AAT TAT TTA TTA GCA CAA     589
Lys Gly Ile Asp Gly Leu Val Leu Gly Ala Asn Tyr Leu Leu Ala Gln
160                 165                 170                 175

AAG CGT GAG GGT GCA AAA GGT GAA AAT AAG CGG CCT AAT GAT AAG GCT     637
Lys Arg Glu Gly Ala Lys Gly Glu Asn Lys Arg Pro Asn Asp Lys Ala
                180                 185                 190
```

```
GGT GAA GTA CGT ATA GGT GAA ATC AAT AAT GGA ATT CAA GTT GGT GCA        685
Gly Glu Val Arg Ile Gly Glu Ile Asn Asn Gly Ile Gln Val Gly Ala
            195                 200                 205

AAA TAT GAT GCA AAC GAC ATC GTT GCA AAA ATT GCT TAT GGT AGA ACT        733
Lys Tyr Asp Ala Asn Asp Ile Val Ala Lys Ile Ala Tyr Gly Arg Thr
            210                 215                 220

AAC TAC AAA TAT AAC GAA TCT GAC GAG CAT AAA CAG CAA TTA AAT GGT        781
Asn Tyr Lys Tyr Asn Glu Ser Asp Glu His Lys Gln Gln Leu Asn Gly
            225                 230                 235

GTA TTA GCA ACT TTA GGC TAT CGT TTT AGT GAT TTA GGC TTA TTA GTG        829
Val Leu Ala Thr Leu Gly Tyr Arg Phe Ser Asp Leu Gly Leu Leu Val
240                 245                 250                 255

TCT CTA GAT AGT GGC TAT GCA AAA ACT AAA AAC TAT AAA ATT AAA CAC        877
Ser Leu Asp Ser Gly Tyr Ala Lys Thr Lys Asn Tyr Lys Ile Lys His
            260                 265                 270

GAA AAA CGC TAT TTC GTA TCT CCA GGT TTC CAA TAT GAA TTA ATG GAA        925
Glu Lys Arg Tyr Phe Val Ser Pro Gly Phe Gln Tyr Glu Leu Met Glu
            275                 280                 285

GAT ACT AAT GTC TAT GGC AAC TTC AAA TAT GAA CGC ACT TCT GTA GAT        973
Asp Thr Asn Val Tyr Gly Asn Phe Lys Tyr Glu Arg Thr Ser Val Asp
            290                 295                 300

CAA GGT GAA AAA ACA CGT GAA CAA GCA GTA TTA TTC GGT GTA GAT CAT       1021
Gln Gly Glu Lys Thr Arg Glu Gln Ala Val Leu Phe Gly Val Asp His
            305                 310                 315

AAA CTT CAC AAA CAA CTA TTA ACC TAT ATT GAA GGT GCT TAC GCT AGA       1069
Lys Leu His Lys Gln Leu Leu Thr Tyr Ile Glu Gly Ala Tyr Ala Arg
320                 325                 330                 335

ACT AGA ACA ACT GAG ACA GGT AAA GGC GTA AAA ACT GAA AAA GAA AAA       1117
Thr Arg Thr Thr Glu Thr Gly Lys Gly Val Lys Thr Glu Lys Glu Lys
            340                 345                 350

TCA GTG GGT GTA GGT TTA CGC GTT TAC TTC TAATCATTTG TTAGAAATAC         1167
Ser Val Gly Val Gly Leu Arg Val Tyr Phe
            355                 360

ATTATTAAAA GCAAGGCGAA TCGAAAGATT CGCTTTTTTT GCTCAAAATC AAGTTAAAAA     1227

ATGATTAAGT TAAAAGTGTA TAAATATTTA GGCTATTTTA TAAGTAACAA AATATTAATA     1287

AAAAATCTGT GACATATATC ACAGATTTTT AAATCAATTA ACTATTTAAG TGTTTACTAT     1347

TAATTCTCTT TCCACTTTCC GTTTACTACT GTGCCGATTA CTTGGTAATT TGGCGTAAAC     1407

ACGGCTAAGT TTGCTATCTT ACCTTTTTCT ACCGAACCTA AACGATCATC TATACCAATT     1467

GCTCGTCGAC                                                           1477

(2) INFORMATION FOR SEQ ID NO:8:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:8:

Met Lys Lys Thr Leu Ala Ala Leu Ile Val Gly Ala Phe Ala Ala Ser
 1               5                  10                  15

Ala Ala Asn Ala Ala Val Val Tyr Asn Asn Glu Gly Thr Asn Val Glu
            20                  25                  30

Leu Gly Gly Arg Leu Ser Ile Ile Ala Glu Gln Ser Asn Ser Thr Val
        35                  40                  45

Asp Asn Gln Lys Gln Gln His Gly Ala Leu Arg Asn Gln Gly Ser Arg
```

-continued

```
                50                      55                      60
        Phe His Ile Lys Ala Thr His Asn Phe Gly Asp Gly Phe Tyr Ala Gln
            65                      70                      75                  80

Gly Tyr Leu Glu Thr Arg Phe Val Thr Lys Ala Ser Glu Asn Gly Ser
                            85                      90                      95

Asp Asn Phe Gly Asp Ile Thr Ser Lys Tyr Ala Tyr Val Thr Leu Gly
                        100                     105                     110

Asn Lys Ala Phe Gly Glu Val Lys Leu Gly Arg Ala Lys Thr Ile Ala
                    115                     120                     125

Asp Gly Ile Thr Ser Ala Glu Asp Lys Glu Tyr Gly Val Leu Asn Asn
                130                     135                     140

Ser Asp Tyr Ile Pro Thr Ser Gly Asn Thr Val Gly Tyr Thr Phe Lys
        145                     150                     155                 160

Gly Ile Asp Gly Leu Val Leu Gly Ala Asn Tyr Leu Leu Ala Gln Lys
                            165                     170                     175

Arg Glu Gly Ala Lys Gly Glu Asn Lys Arg Pro Asn Asp Lys Ala Gly
                        180                     185                     190

Glu Val Arg Ile Gly Glu Ile Asn Asn Gly Ile Gln Val Gly Ala Lys
                    195                     200                     205

Tyr Asp Ala Asn Asp Ile Val Ala Lys Ile Ala Tyr Gly Arg Thr Asn
                210                     215                     220

Tyr Lys Tyr Asn Glu Ser Asp Glu His Lys Gln Gln Leu Asn Gly Val
        225                     230                     235                 240

Leu Ala Thr Leu Gly Tyr Arg Phe Ser Asp Leu Gly Leu Leu Val Ser
                            245                     250                     255

Leu Asp Ser Gly Tyr Ala Lys Thr Lys Asn Tyr Lys Ile Lys His Glu
                        260                     265                     270

Lys Arg Tyr Phe Val Ser Pro Gly Phe Gln Tyr Glu Leu Met Glu Asp
                    275                     280                     285

Thr Asn Val Tyr Gly Asn Phe Lys Tyr Glu Arg Thr Ser Val Asp Gln
                290                     295                     300

Gly Glu Lys Thr Arg Glu Gln Ala Val Leu Phe Gly Val Asp His Lys
        305                     310                     315                 320

Leu His Lys Gln Leu Leu Thr Tyr Ile Glu Gly Ala Tyr Ala Arg Thr
                            325                     330                     335

Arg Thr Thr Glu Thr Gly Lys Gly Val Lys Thr Glu Lys Glu Lys Ser
                        340                     345                     350

Val Gly Val Gly Leu Arg Val Tyr Phe
                    355                     360

(2) INFORMATION FOR SEQ ID NO:9:

(i) SEQUENCE CHARACTERISTICS:
        (A) LENGTH: 1137 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 4..1092

(xi) SEQUENCE DESCRIPTION: SEQ ID NO:9:

CAT ATG GCT AGC ATG ACT GGT GGA CAG CAA ATG GGT CGG GAT TCA AGC          48
    Met Ala Ser Met Thr Gly Gly Gln Gln Met Gly Arg Asp Ser Ser
      1               5                  10                  15

TTG GTA CCG AGC TCG GAT CCA GCT GTT GTT TAT AAC AAC GAA GGG ACT          96
```

```
                Leu Val Pro Ser Ser Asp Pro Ala Val Val Tyr Asn Asn Glu Gly Thr
                             20                  25                  30

AAC GTA GAA TTA GGT GGT CGT TTA AGC ATT ATC GCA GAA CAA AGT AAT          144
Asn Val Glu Leu Gly Gly Arg Leu Ser Ile Ile Ala Glu Gln Ser Asn
             35                  40                  45

AGC ACT GTA GAT AAT CAA AAA CAG CAA CAC GGT GCA TTA CGC AAT CAA          192
Ser Thr Val Asp Asn Gln Lys Gln Gln His Gly Ala Leu Arg Asn Gln
             50                  55                  60

GGT TCA CGT TTC CAC ATT AAA GCA ACT CAT AAC TTC GGT GAT GGT TTC          240
Gly Ser Arg Phe His Ile Lys Ala Thr His Asn Phe Gly Asp Gly Phe
     65                  70                  75

TAT GCA CAA GGT TAT TTA GAA ACT CGT TTT GTT ACA AAA GCC TCT GAA          288
Tyr Ala Gln Gly Tyr Leu Glu Thr Arg Phe Val Thr Lys Ala Ser Glu
 80                  85                  90                  95

AAC GGT TCA GAT AAC TTC GGT GAT ATT ACA AGC AAA TAT GCT TAT GTT          336
Asn Gly Ser Asp Asn Phe Gly Asp Ile Thr Ser Lys Tyr Ala Tyr Val
                100                 105                 110

ACT TTA GGA AAT AAA GCA TTC GGT GAA GTA AAA CTT GGT CGT GCG AAA          384
Thr Leu Gly Asn Lys Ala Phe Gly Glu Val Lys Leu Gly Arg Ala Lys
             115                 120                 125

ACT ATT GCT GAT GGC ATA ACA AGT GCA GAA GAT AAA GAA TAT GGC GTT          432
Thr Ile Ala Asp Gly Ile Thr Ser Ala Glu Asp Lys Glu Tyr Gly Val
             130                 135                 140

CTC AAC AAT AGT GAC TAT ATT CCT ACT AGT GGT AAT ACG GTT GGC TAT          480
Leu Asn Asn Ser Asp Tyr Ile Pro Thr Ser Gly Asn Thr Val Gly Tyr
145                 150                 155

ACT TTT AAA GGT ATT GAT GGT TTA GTA TTA GGC GCT AAT TAT TTA TTA          528
Thr Phe Lys Gly Ile Asp Gly Leu Val Leu Gly Ala Asn Tyr Leu Leu
160                 165                 170                 175

GCA CAA AAG CGT GAG GGT GCA AAA GGT GAA AAT AAG CGG CCT AAT GAT          576
Ala Gln Lys Arg Glu Gly Ala Lys Gly Glu Asn Lys Arg Pro Asn Asp
             180                 185                 190

AAG GCT GGT GAA GTA CGT ATA GGT GAA ATC AAT AAT GGA ATT CAA GTT          624
Lys Ala Gly Glu Val Arg Ile Gly Glu Ile Asn Asn Gly Ile Gln Val
             195                 200                 205

GGT GCA AAA TAT GAT GCA AAC GAC ATC GTT GCA AAA ATT GCT TAT GGT          672
Gly Ala Lys Tyr Asp Ala Asn Asp Ile Val Ala Lys Ile Ala Tyr Gly
             210                 215                 220

AGA ACT AAC TAC AAA TAT AAC GAA TCT GAC GAG CAT AAA CAG CAA TTA          720
Arg Thr Asn Tyr Lys Tyr Asn Glu Ser Asp Glu His Lys Gln Gln Leu
     225                 230                 235

AAT GGT GTA TTA GCA ACT TTA GGC TAT CGT TTT AGT GAT TTA GGC TTA          768
Asn Gly Val Leu Ala Thr Leu Gly Tyr Arg Phe Ser Asp Leu Gly Leu
240                 245                 250                 255

TTA GTG TCT CTA GAT AGT GGC TAT GCA AAA ACT AAA AAC TAT AAA ATT          816
Leu Val Ser Leu Asp Ser Gly Tyr Ala Lys Thr Lys Asn Tyr Lys Ile
             260                 265                 270

AAA CAC GAA AAA CGC TAT TTC GTA TCT CCA GGT TTC CAA TAT GAA TTA          864
Lys His Glu Lys Arg Tyr Phe Val Ser Pro Gly Phe Gln Tyr Glu Leu
             275                 280                 285

ATG GAA GAT ACT AAT GTC TAT GGC AAC TTC AAA TAT GAA CGC ACT TCT          912
Met Glu Asp Thr Asn Val Tyr Gly Asn Phe Lys Tyr Glu Arg Thr Ser
             290                 295                 300

GTA GAT CAA GGT GAA AAA ACA CGT GAA CAA GCA GTA TTA TTC GGT GTA          960
Val Asp Gln Gly Glu Lys Thr Arg Glu Gln Ala Val Leu Phe Gly Val
     305                 310                 315

GAT CAT AAA CTT CAC AAA CAA CTA TTA ACC TAT ATT GAA GGT GCT TAC         1008
Asp His Lys Leu His Lys Gln Leu Leu Thr Tyr Ile Glu Gly Ala Tyr
320                 325                 330                 335
```

```
GCT AGA ACT AGA ACA ACT GAG ACA GGT AAA GGC GTA AAA ACT GAA AAA      1056
Ala Arg Thr Arg Thr Thr Glu Thr Gly Lys Gly Val Lys Thr Glu Lys
            340                 345                 350

GAA AAA TCA GTG GGT GTA GGT TTA CGC GTT TAC TTC TAATCATTTG           1102
Glu Lys Ser Val Gly Val Gly Leu Arg Val Tyr Phe
            355                 360

TTAGAAATAC ATTATTAAAA GCAAGGCGAC TCGAG                               1137
```

(2) INFORMATION FOR SEQ ID NO:10:

(i) SEQUENCE CHARACTERISTICS:
        (A) LENGTH: 363 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Ser Met Thr Gly Gly Gln Gln Met Gly Arg Asp Ser Ser Leu
 1               5                  10                  15

Val Pro Ser Ser Asp Pro Ala Val Tyr Asn Asn Glu Gly Thr Asn
            20                  25                  30

Val Glu Leu Gly Gly Arg Leu Ser Ile Ile Ala Glu Gln Ser Asn Ser
        35                  40                  45

Thr Val Asp Asn Gln Lys Gln His Gly Ala Leu Arg Asn Gln Gly
    50                  55                  60

Ser Arg Phe His Ile Lys Ala Thr His Asn Phe Gly Asp Gly Phe Tyr
 65                  70                  75                  80

Ala Gln Gly Tyr Leu Glu Thr Arg Phe Val Thr Lys Ala Ser Glu Asn
                85                  90                  95

Gly Ser Asp Asn Phe Gly Asp Ile Thr Ser Lys Tyr Ala Tyr Val Thr
            100                 105                 110

Leu Gly Asn Lys Ala Phe Gly Glu Val Lys Leu Gly Arg Ala Lys Thr
        115                 120                 125

Ile Ala Asp Gly Ile Thr Ser Ala Glu Asp Lys Glu Tyr Gly Val Leu
    130                 135                 140

Asn Asn Ser Asp Tyr Ile Pro Thr Ser Gly Asn Thr Val Gly Tyr Thr
145                 150                 155                 160

Phe Lys Gly Ile Asp Gly Leu Val Leu Gly Ala Asn Tyr Leu Leu Ala
                165                 170                 175

Gln Lys Arg Glu Gly Ala Lys Gly Glu Asn Lys Arg Pro Asn Asp Lys
            180                 185                 190

Ala Gly Glu Val Arg Ile Gly Glu Ile Asn Asn Gly Ile Gln Val Gly
        195                 200                 205

Ala Lys Tyr Asp Ala Asn Asp Ile Val Ala Lys Ile Ala Tyr Gly Arg
    210                 215                 220

Thr Asn Tyr Lys Tyr Asn Glu Ser Asp Glu His Lys Gln Gln Leu Asn
225                 230                 235                 240

Gly Val Leu Ala Thr Leu Gly Tyr Arg Phe Ser Asp Leu Gly Leu Leu
                245                 250                 255

Val Ser Leu Asp Ser Gly Tyr Ala Lys Thr Lys Asn Tyr Lys Ile Lys
            260                 265                 270

His Glu Lys Arg Tyr Phe Val Ser Pro Gly Phe Gln Tyr Glu Leu Met
        275                 280                 285

Glu Asp Thr Asn Val Tyr Gly Asn Phe Lys Tyr Glu Arg Thr Ser Val
    290                 295                 300
```

-continued

```
Asp Gln Gly Glu Lys Thr Arg Glu Gln Ala Val Leu Phe Gly Val Asp
305                 310                 315                 320

His Lys Leu His Lys Gln Leu Leu Thr Tyr Ile Glu Gly Ala Tyr Ala
            325                 330                 335

Arg Thr Arg Thr Thr Glu Thr Gly Lys Gly Val Lys Thr Glu Lys Glu
            340                 345                 350

Lys Ser Val Gly Val Gly Leu Arg Val Tyr Phe
355                 360
```

(2) INFORMATION FOR SEQ ID NO:11:

(i) SEQUENCE CHARACTERISTICS:
        (A) LENGTH: 1074 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 4..1029

(xi) SEQUENCE DESCRIPTION: SEQ ID NO:11:

```
CAT ATG GCT GTT GTT TAT AAC AAC GAA GGG ACT AAC GTA GAA TTA GGT        48
    Met Ala Val Val Tyr Asn Asn Glu Gly Thr Asn Val Glu Leu Gly
    1               5                   10                  15

GGT CGT TTA AGC ATT ATC GCA GAA CAA AGT AAT AGC ACT GTA GAT AAT        96
Gly Arg Leu Ser Ile Ile Ala Glu Gln Ser Asn Ser Thr Val Asp Asn
                20                  25                  30

CAA AAA CAG CAA CAC GGT GCA TTA CGC AAT CAA GGT TCA CGT TTC CAC       144
Gln Lys Gln Gln His Gly Ala Leu Arg Asn Gln Gly Ser Arg Phe His
            35                  40                  45

ATT AAA GCA ACT CAT AAC TTC GGT GAT GGT TTC TAT GCA CAA GGT TAT       192
Ile Lys Ala Thr His Asn Phe Gly Asp Gly Phe Tyr Ala Gln Gly Tyr
        50                  55                  60

TTA GAA ACT CGT TTT GTT ACA AAA GCC TCT GAA AAC GGT TCA GAT AAC       240
Leu Glu Thr Arg Phe Val Thr Lys Ala Ser Glu Asn Gly Ser Asp Asn
65                  70                  75

TTC GGT GAT ATT ACA AGC AAA TAT GCT TAT GTT ACT TTA GGA AAT AAA       288
Phe Gly Asp Ile Thr Ser Lys Tyr Ala Tyr Val Thr Leu Gly Asn Lys
80                  85                  90                  95

GCA TTC GGT GAA GTA AAA CTT GGT CGT GCG AAA ACT ATT GCT GAT GGC       336
Ala Phe Gly Glu Val Lys Leu Gly Arg Ala Lys Thr Ile Ala Asp Gly
                100                 105                 110

ATA ACA AGT GCA GAA GAT AAA GAA TAT GGC GTT CTC AAC AAT AGT GAC       384
Ile Thr Ser Ala Glu Asp Lys Glu Tyr Gly Val Leu Asn Asn Ser Asp
            115                 120                 125

TAT ATT CCT ACT AGT GGT AAT ACG GTT GGC TAT ACT TTT AAA GGT ATT       432
Tyr Ile Pro Thr Ser Gly Asn Thr Val Gly Tyr Thr Phe Lys Gly Ile
        130                 135                 140

GAT GGT TTA GTA TTA GGC GCT AAT TAT TTA TTA GCA CAA AAG CGT GAG       480
Asp Gly Leu Val Leu Gly Ala Asn Tyr Leu Leu Ala Gln Lys Arg Glu
145                 150                 155

GGT GCA AAA GGT GAA AAT AAG CGG CCT AAT GAT AAG GCT GGT GAA GTA       528
Gly Ala Lys Gly Glu Asn Lys Arg Pro Asn Asp Lys Ala Gly Glu Val
160                 165                 170                 175

CGT ATA GGT GAA ATC AAT AAT GGA ATT CAA GTT GGT GCA AAA TAT GAT       576
Arg Ile Gly Glu Ile Asn Asn Gly Ile Gln Val Gly Ala Lys Tyr Asp
                180                 185                 190

GCA AAC GAC ATC GTT GCA AAA ATT GCT TAT GGT AGA ACT AAC TAC AAA       624
Ala Asn Asp Ile Val Ala Lys Ile Ala Tyr Gly Arg Thr Asn Tyr Lys
            195                 200                 205
```

```
TAT AAC GAA TCT GAC GAG CAT AAA CAG CAA TTA AAT GGT GTA TTA GCA       672
Tyr Asn Glu Ser Asp Glu His Lys Gln Gln Leu Asn Gly Val Leu Ala
        210                 215                 220

ACT TTA GGC TAT CGT TTT AGT GAT TTA GGC TTA TTA GTG TCT CTA GAT       720
Thr Leu Gly Tyr Arg Phe Ser Asp Leu Gly Leu Leu Val Ser Leu Asp
225                 230                 235

AGT GGC TAT GCA AAA ACT AAA AAC TAT AAA ATT AAA CAC GAA AAA CGC       768
Ser Gly Tyr Ala Lys Thr Lys Asn Tyr Lys Ile Lys His Glu Lys Arg
240                 245                 250                 255

TAT TTC GTA TCT CCA GGT TTC CAA TAT GAA TTA ATG GAA GAT ACT AAT       816
Tyr Phe Val Ser Pro Gly Phe Gln Tyr Glu Leu Met Glu Asp Thr Asn
                260                 265                 270

GTC TAT GGC AAC TTC AAA TAT GAA CGC ACT TCT GTA GAT CAA GGT GAA       864
Val Tyr Gly Asn Phe Lys Tyr Glu Arg Thr Ser Val Asp Gln Gly Glu
            275                 280                 285

AAA ACA CGT GAA CAA GCA GTA TTA TTC GGT GTA GAT CAT AAA CTT CAC       912
Lys Thr Arg Glu Gln Ala Val Leu Phe Gly Val Asp His Lys Leu His
        290                 295                 300

AAA CAA CTA TTA ACC TAT ATT GAA GGT GCT TAC GCT AGA ACT AGA ACA       960
Lys Gln Leu Leu Thr Tyr Ile Glu Gly Ala Tyr Ala Arg Thr Arg Thr
    305                 310                 315

ACT GAG ACA GGT AAA GGC GTA AAA ACT GAA AAA GAA AAA TCA GTG GGT      1008
Thr Glu Thr Gly Lys Gly Val Lys Thr Glu Lys Glu Lys Ser Val Gly
320                 325                 330                 335

GTA GGT TTA CGC GTT TAC TTC TAATCATTTG TTAGAAATAC ATTATTAAAA         1059
Val Gly Leu Arg Val Tyr Phe
                340

GCAAGGCGAC TCGAG                                                     1074

(2) INFORMATION FOR SEQ ID NO:12:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO:12:

Met Ala Val Val Tyr Asn Asn Glu Gly Thr Asn Val Glu Leu Gly Gly
 1               5                  10                  15

Arg Leu Ser Ile Ile Ala Glu Gln Ser Asn Ser Thr Val Asp Asn Gln
             20                  25                  30

Lys Gln Gln His Gly Ala Leu Arg Asn Gln Gly Ser Arg Phe His Ile
         35                  40                  45

Lys Ala Thr His Asn Phe Gly Asp Gly Phe Tyr Ala Gln Gly Tyr Leu
     50                  55                  60

Glu Thr Arg Phe Val Thr Lys Ala Ser Glu Asn Gly Ser Asp Asn Phe
 65                  70                  75                  80

Gly Asp Ile Thr Ser Lys Tyr Ala Tyr Val Thr Leu Gly Asn Lys Ala
                 85                  90                  95

Phe Gly Glu Val Lys Leu Gly Arg Ala Lys Thr Ile Ala Asp Gly Ile
             100                 105                 110

Thr Ser Ala Glu Asp Lys Glu Tyr Gly Val Leu Asn Asn Ser Asp Tyr
         115                 120                 125

Ile Pro Thr Ser Gly Asn Thr Val Gly Tyr Thr Phe Lys Gly Ile Asp
     130                 135                 140

Gly Leu Val Leu Gly Ala Asn Tyr Leu Leu Ala Gln Lys Arg Glu Gly
145                 150                 155                 160
```

```
            Ala Lys Gly Glu Asn Lys Arg Pro Asn Asp Lys Ala Gly Glu Val Arg
                            165                 170                 175

Ile Gly Glu Ile Asn Asn Gly Ile Gln Val Gly Ala Lys Tyr Asp Ala
                        180                 185                 190

Asn Asp Ile Val Ala Lys Ile Ala Tyr Gly Arg Thr Asn Tyr Lys Tyr
                        195                 200                 205

Asn Glu Ser Asp Glu His Lys Gln Gln Leu Asn Gly Val Leu Ala Thr
                    210                 215                 220

Leu Gly Tyr Arg Phe Ser Asp Leu Gly Leu Leu Val Ser Leu Asp Ser
            225                 230                 235                 240

Gly Tyr Ala Lys Thr Lys Asn Tyr Lys Ile Lys His Glu Lys Arg Tyr
                            245                 250                 255

Phe Val Ser Pro Gly Phe Gln Tyr Glu Leu Met Glu Asp Thr Asn Val
                        260                 265                 270

Tyr Gly Asn Phe Lys Tyr Glu Arg Thr Ser Val Asp Gln Gly Glu Lys
                        275                 280                 285

Thr Arg Glu Gln Ala Val Leu Phe Gly Val Asp His Lys Leu His Lys
                    290                 295                 300

Gln Leu Leu Thr Tyr Ile Glu Gly Ala Tyr Ala Arg Thr Arg Thr Thr
            305                 310                 315                 320

Glu Thr Gly Lys Gly Val Lys Thr Glu Lys Glu Lys Ser Val Gly Val
                            325                 330                 335

Gly Leu Arg Val Tyr Phe
                            340

(2) INFORMATION FOR SEQ ID NO:13:

(i) SEQUENCE CHARACTERISTICS:
        (A) LENGTH: 1072 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 4..1029

(xi) SEQUENCE DESCRIPTION: SEQ ID NO:13:

CAT ATG GCT GTT GTT TAT AAC AAC GAA GGG ACT AAC GTA GAA TTA GGT        48
    Met Ala Val Val Tyr Asn Asn Glu Gly Thr Asn Val Glu Leu Gly
    1               5                  10                  15

GGT CGT TTA AGC ATT ATC GCA GAA CAA AGT AAT AGC ACT GTA GAT AAT        96
Gly Arg Leu Ser Ile Ile Ala Glu Gln Ser Asn Ser Thr Val Asp Asn
                20                  25                  30

CAA AAA CAG CAA CAC GGT GCA TTA CGC AAT CAA GGT TCA CGT TTC CAC       144
Gln Lys Gln Gln His Gly Ala Leu Arg Asn Gln Gly Ser Arg Phe His
            35                  40                  45

ATT AAA GCA ACT CAT AAC TTC GGT GAT GGT TTC TAT GCA CAA GGT TAT       192
Ile Lys Ala Thr His Asn Phe Gly Asp Gly Phe Tyr Ala Gln Gly Tyr
        50                  55                  60

TTA GAA ACT CGT TTT GTT ACA AAA GCC TCT GAA AAC GGT TCA GAT AAC       240
Leu Glu Thr Arg Phe Val Thr Lys Ala Ser Glu Asn Gly Ser Asp Asn
65                  70                  75

TTC GGT GAT ATT ACA AGC AAA TAT GCT TAT GTT ACT TTA GGA AAT AAA       288
Phe Gly Asp Ile Thr Ser Lys Tyr Ala Tyr Val Thr Leu Gly Asn Lys
    80                  85                  90                  95

GCA TTC GGT GAA GTA AAA CTT GGT CGT GCG AAA ACT ATT GCT GAT GGC       336
Ala Phe Gly Glu Val Lys Leu Gly Arg Ala Lys Thr Ile Ala Asp Gly
            100                 105                 110
```

```
ATA ACA AGT GCA GAA GAT AAA GAA TAT GGC GTT CTC AAC AAT AGT GAC    384
Ile Thr Ser Ala Glu Asp Lys Glu Tyr Gly Val Leu Asn Asn Ser Asp
            115                 120                 125

TAT ATT CCT ACT AGT GGT AAT ACG GTT GGC TAT ACT TTT AAA GGT ATT    432
Tyr Ile Pro Thr Ser Gly Asn Thr Val Gly Tyr Thr Phe Lys Gly Ile
        130                 135                 140

GAT GGT TTA GTA TTA GGC GCT AAT TAT TTA TTA GCA CAA AAG CGT GAG    480
Asp Gly Leu Val Leu Gly Ala Asn Tyr Leu Leu Ala Gln Lys Arg Glu
145                 150                 155

GGT GCA AAA GGT GAA AAT AAG CGG CCT AAT GAT AAG GCT GGT GAA GTA    528
Gly Ala Lys Gly Glu Asn Lys Arg Pro Asn Asp Lys Ala Gly Glu Val
160                 165                 170                 175

CGT ATA GGT GAA ATC AAT AAT GGA ATT CAA GTT GGT GCA AAA TAT GAT    576
Arg Ile Gly Glu Ile Asn Asn Gly Ile Gln Val Gly Ala Lys Tyr Asp
                180                 185                 190

GCA AAC GAC ATC GTT GCA AAA ATT GCT TAT GGT AGA ACT AAC TAC AAA    624
Ala Asn Asp Ile Val Ala Lys Ile Ala Tyr Gly Arg Thr Asn Tyr Lys
            195                 200                 205

TAT AAC GAA TCT GAC GAG CAT AAA CAG CAA TTA AAT GGT GTA TTA GCA    672
Tyr Asn Glu Ser Asp Glu His Lys Gln Gln Leu Asn Gly Val Leu Ala
        210                 215                 220

ACT TTA GGC TAT CGT TTT AGT GAT TTA GGC TTA TTA GTG TCT CTA GAT    720
Thr Leu Gly Tyr Arg Phe Ser Asp Leu Gly Leu Leu Val Ser Leu Asp
    225                 230                 235

AGT GGC TAT GCA AAA ACT AAA AAC TAT AAA ATT AAA CAC GAA AAA CGC    768
Ser Gly Tyr Ala Lys Thr Lys Asn Tyr Lys Ile Lys His Glu Lys Arg
240                 245                 250                 255

TAT TTC GTA TCT CCA GGT TTC CAA TAT GAA TTA ATG GAA GAT ACT AAT    816
Tyr Phe Val Ser Pro Gly Phe Gln Tyr Glu Leu Met Glu Asp Thr Asn
                260                 265                 270

GTC TAT GGC AAC TTC AAA TAT GAA CGC ACT TCT GTA GAT CAA GGT GAA    864
Val Tyr Gly Asn Phe Lys Tyr Glu Arg Thr Ser Val Asp Gln Gly Glu
            275                 280                 285

AAA ACA CGT GAA CAA GCA GTA TTA TTC GGT GTA GAT CAT AAA CTT CAC    912
Lys Thr Arg Glu Gln Ala Val Leu Phe Gly Val Asp His Lys Leu His
        290                 295                 300

AAA CAA CTA TTA ACC TAT ATT GAA GGT GCT TAC GCT AGA ACT AGA ACA    960
Lys Gln Leu Leu Thr Tyr Ile Glu Gly Ala Tyr Ala Arg Thr Arg Thr
    305                 310                 315

ACT GAG ACA GGT AAA GGC GTA AAA ACT GAA AAA GAA AAA TCA GTG GGT   1008
Thr Glu Thr Gly Lys Gly Val Lys Thr Glu Lys Glu Lys Ser Val Gly
320                 325                 330                 335

GTA GGT TTA CGC GTT TAC TTC TAATCATTTG TTAGAAATAC ATTATTAAAA      1059
Val Gly Leu Arg Val Tyr Phe
                340

GCAAGGCGGA TCC                                                    1072
```

(2) INFORMATION FOR SEQ ID NO:14:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ala Val Val Tyr Asn Asn Glu Gly Thr Asn Val Glu Leu Gly Gly
  1               5                  10                  15

Arg Leu Ser Ile Ile Ala Glu Gln Ser Asn Ser Thr Val Asp Asn Gln
```

```
                       20                  25                  30
Lys Gln Gln His Gly Ala Leu Arg Asn Gln Gly Ser Arg Phe His Ile
            35                  40                  45

Lys Ala Thr His Asn Phe Gly Asp Gly Phe Tyr Ala Gln Gly Tyr Leu
 50                      55                  60

Glu Thr Arg Phe Val Thr Lys Ala Ser Glu Asn Gly Ser Asp Asn Phe
 65                  70                  75                   80

Gly Asp Ile Thr Ser Lys Tyr Ala Tyr Val Thr Leu Gly Asn Lys Ala
             85                  90                  95

Phe Gly Glu Val Lys Leu Gly Arg Ala Lys Thr Ile Ala Asp Gly Ile
            100                 105                 110

Thr Ser Ala Glu Asp Lys Glu Tyr Gly Val Leu Asn Asn Ser Asp Tyr
            115                 120                 125

Ile Pro Thr Ser Gly Asn Thr Val Gly Tyr Thr Phe Lys Gly Ile Asp
    130                 135                 140

Gly Leu Val Leu Gly Ala Asn Tyr Leu Leu Ala Gln Lys Arg Glu Gly
145                 150                 155                 160

Ala Lys Gly Glu Asn Lys Arg Pro Asn Asp Lys Ala Gly Glu Val Arg
            165                 170                 175

Ile Gly Glu Ile Asn Asn Gly Ile Gln Val Gly Ala Lys Tyr Asp Ala
            180                 185                 190

Asn Asp Ile Val Ala Lys Ile Ala Tyr Gly Arg Thr Asn Tyr Lys Tyr
            195                 200                 205

Asn Glu Ser Asp Glu His Lys Gln Gln Leu Asn Gly Val Leu Ala Thr
    210                 215                 220

Leu Gly Tyr Arg Phe Ser Asp Leu Gly Leu Leu Val Ser Leu Asp Ser
225                 230                 235                 240

Gly Tyr Ala Lys Thr Lys Asn Tyr Lys Ile Lys His Glu Lys Arg Tyr
            245                 250                 255

Phe Val Ser Pro Gly Phe Gln Tyr Glu Leu Met Glu Asp Thr Asn Val
            260                 265                 270

Tyr Gly Asn Phe Lys Tyr Glu Arg Thr Ser Val Asp Gln Gly Glu Lys
    275                 280                 285

Thr Arg Glu Gln Ala Val Leu Phe Gly Val Asp His Lys Leu His Lys
    290                 295                 300

Gln Leu Leu Thr Tyr Ile Glu Gly Ala Tyr Ala Arg Thr Arg Thr Thr
305                 310                 315                 320

Glu Thr Gly Lys Gly Val Lys Thr Glu Lys Glu Lys Ser Val Gly Val
            325                 330                 335

Gly Leu Arg Val Tyr Phe
            340
```

METHOD FOR THE HIGH LEVEL EXPRESSION, PURIFICATION AND REFOLDING OF THE OUTER MEMBRANE PROTEIN P2 FROM *HAEMOPHILUS INFLUENZAE* TYPE B

BACKGROUND OF THE INVENTION

1. Field of the Invention

The present invention is in the field of recombinant DNA technology, protein expression, and vaccines. The present invention relates, in particular, to a method of expressing the outer membrane protein P2 from *Haemophilus influenzae* type b (Hib-P2). The invention also relates to a method of purification and refolding of the recombinant protein.

2. Background Information

*Haemophilus influenzae* type b causes bacterial meningitis and other invasive infections in children under the age of 4 years in the United States. The P2 protein from several *H. influenzae* type b strains has been purified and characterized (Munson et al., *J. Clin. Invest.* 72:677–684 (1983) and Vachon et al., *J. Bacteriol.* 162:918–924 (1985)). The structural gene encoding the P2 protein type 1H has been cloned and the DNA sequence determined (Hansen, E. J. et al., *Infection and Immunity* 56:2709–2716 (October 1988); Hansen, E. J. et al., *Infection and Immunity* 57:1100–1107 (April 1989); and Munson, Jr., R. and Tolan, Jr., R. W., *Infection and Immunity* 57:88–94 (January 1989)).

Although recombinant P2 genes have been expressed in *H. influenzae* Rd (Hansen, E. J. et al., *Infection and Immunity* 56:2709–2716 (October 1988)) and in *E. coli* (Munson, Jr., R. and Tolan, Jr., R. W., *Infection and Immunity* 57:88–94 (January 1989)), the level of expression present in *E. coli* was low, possibly due to the toxicity of the P2 protein in *E. coli* as suggested by Munson (Munson, Jr., R. and Tolan, Jr., R. W., *Infection and Immunity* 57:88–94 (January 1989)) and Hansen (Hansen, E. J. et al., *Infection and Immunity* 56:2709–2716 (October 1988)). The present invention provides a method of expressing Hib-P2 in *E. coli* wherein the Hib-P2 protein comprises more than 2% of the total protein expressed in *E. coli*.

SUMMARY OF THE INVENTION

It is a general object of the invention to provide a method of expressing recombinant outer membrane protein P2 from *Haemophils influenzae* type b (Hib-P2), or a fusion protein thereof, in *E. coli*.

It is a specific object of the invention to provide a method of expressing the outer membrane protein P2 from *Haemophilus influenzae* type b (Hib-P2), or a fusion protein thereof, in *E. coli* comprising:

(a) transforming *E. coli* by a vector comprising a selectable marker and gene coding for a protein selected from the group consisting of
  (i) a mature P2 protein, and
  (ii) a fusion protein comprising a mature P2 protein fused to amino acids 1 to 22 of the T7 gene φ10 capsid protein;
wherein said gene is operably linked to the T7 promoter; and
(b) growing the transformed *E. coli* in LB media containing glucose and a selection agent at about 30° C.,
wherein the protein so produced comprises more than 2% of the total protein expressed in the *E. coli*.

It is another specific object of the invention to provide a method of purifying and refolding an outer membrane protein P2 from *Haemophilus influenzae* type b (Hib-P2), or a fusion protein thereof, produced according to the above-described methods.

It is a further specific object of the invention to provide a vaccine comprising the outer membrane protein P2 from *Haemophilus influenzae* type b (Hib-P2), or a fusion protein thereof, produced according to the above methods, in an amount effective to elicit protective antibodies in an animal to *Haemophilus influenzae* type b; together with a pharmaceutically acceptable diluent, carrier, or excipient.

It is another specific object of the invention to provide the above-described vaccine, wherein said outer membrane protein P2 or fusion protein thereof is conjugated to a Haemophilus capsular polysaccharide.

It is a further specific object of the invention to provide a method of preventing bacterial meningitis in an animal comprising administering to the animal the Hib-P2 protein or fusion protein-vaccine produced according to the above-described methods.

It is another specific object of the invention to provide a method of preparing a polysaccharide conjugate comprising: obtaining the above-described outer membrane protein P2 or fusion protein; obtaining a polysaccharide from a Haemophilus organism; and conjugating the protein to the polysaccharide.

It is another specific object of the invention to provide a method of purifying the above-described outer membrane protein P2 or fusion protein comprising: lysing the transformed *E. coli* to release the P2 protein or fusion protein as part of insoluble inclusion bodies; washing the inclusion bodies with a buffer to remove contaminating *E. coli* cellular proteins; resuspending and dissolving the inclusion bodies in an aqueous solution of a denaturant; diluting the resultant solution in a detergent; and purifying the solubilized P2 protein or fusion protein by gel filtration.

It is another specific object of the invention to provide a method of refolding the above-described outer membrane protein P2 or fusion protein comprising: lysing the transformed *E. coli* to release the P2 protein or fusion protein as part of insoluble inclusion bodies; washing the inclusion bodies with a buffer to remove contaminating *E. coli* cellular proteins; resuspending and dissolving the inclusion bodies in an aqueous solution of a denaturant; diluting the resultant solution in a detergent; and purifying the solubilized P2 protein or fusion protein by gel filtration to give the refolded protein in the eluant and storing the gel filtration product at about 4° C. in an aqueous solution containing high concentrations of NaCl and calcium ions until the outer membrane protein P2 refolds.

Further objects and advantages of the present invention will be clear from the description that follows.

β-mercaptoethanol, and 0.05% bromphenol blue. After boiling the mixture of 5 minutes, the samples were then diluted 1:10 with load buffer and then 10 μl of the diluted sample loaded per lane.

Figure 1:
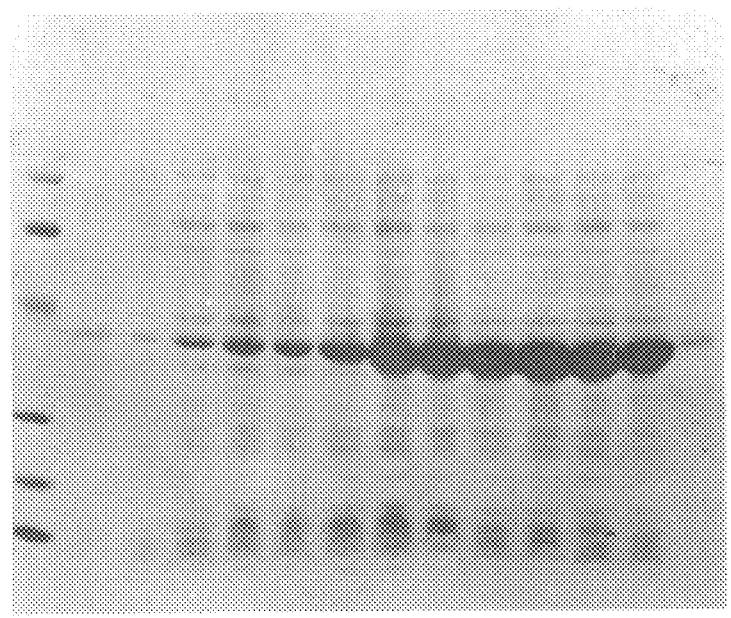
FIG. 1. Electrophoretic gel showing the kinetics of induction of plasmid pNV-3. (Coomassie blue stained linear 8–16% gradient SDS-PAGE (Novex)). Lane 1 shows molecular weight markers: phosphorylase b (97.4 kDa), bovine serum albumin (66 kDa), ovalbumin (45 kDa), carbonic anhydrase (31 kDa), soybean trypsin inhibitor (21.5 kDa) and lysozyme (14.4 kDa). Lanes 2 and 14 show 4 μg samples of purified rHib porin. Lanes 3–13 show samples of *E. coli* extracts obtained from cells removed at 0, 15, 30, 45, 60, 120, 180, 240, 300, 360 and 420 minutes after addition of IPTG to the culture. At each time point, 5 ml of the culture was removed and immediately chilled to 4° C. The cells were then collected by centrifugation and stored at −75° C. A whole cell extract was made by adding 150 μl of Tris-HCl, pH=8.0, 5 M urea, 1% SDS, 30 mM NaCl, 2.5%
Figure 2:
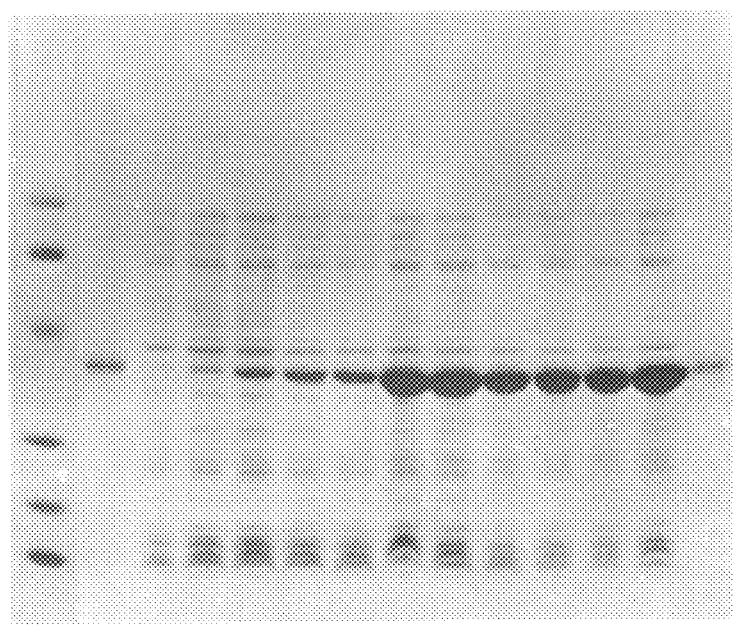

FIG. 2. Electrophoretic gel showing the kinetics of induction of plasmid pNV-6. (Coomassie blue stained linear 8–16% gradient SDS-PAGE (Novex)). Lane 1 shows molecular weight markers: phosphorylase b (97.4 kDa), bovine serum albumin (66 kDa), ovalbumin (45 kDa), carbonic anhydrase (31 kDa), soybean trypsin inhibitor (21.5 kDa) and lysozyme (14.4 kDa). Lanes 2 and 14 show 4 μg samples of purified rHib porin. Lanes 3–13 show samples of E. coli extracts obtained from cells removed at 0, 15, 30, 45, 60, 120, 180, 240, 300, 360 and 420 minutes after addition of IPTG to the culture. At each time point, 5 ml of the culture was removed and immediately chilled to 4° C. The cells were then collected by centrifugation and stored at −75° C. A whole cell extract was made as described in FIG. 1.

Figure 3A:
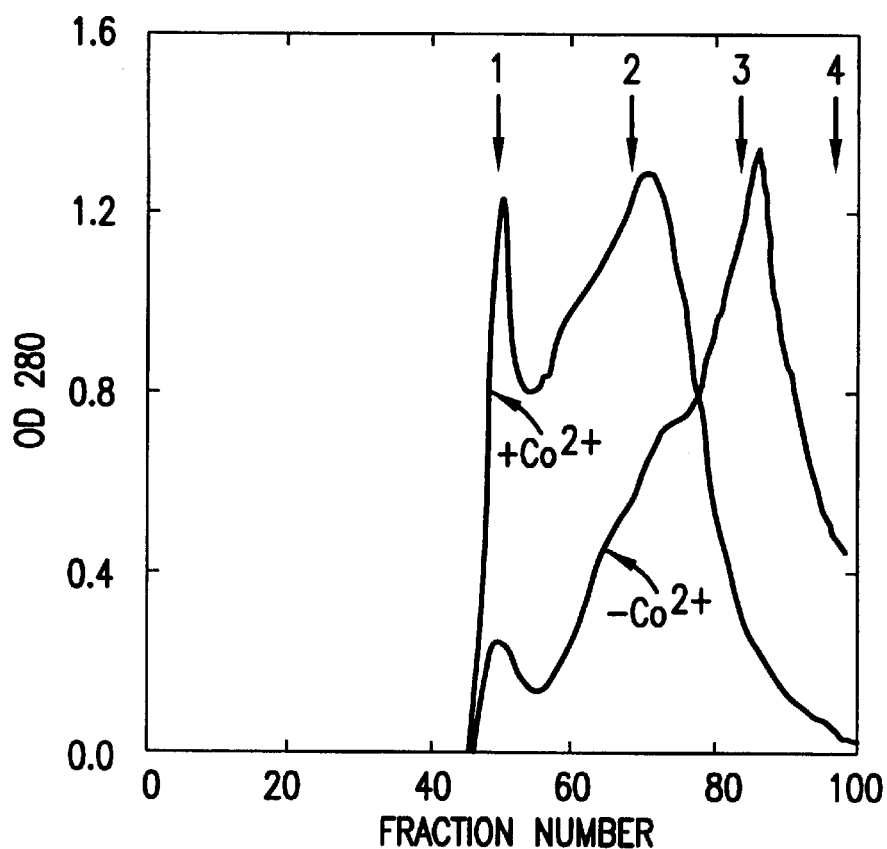
Figure 3B:
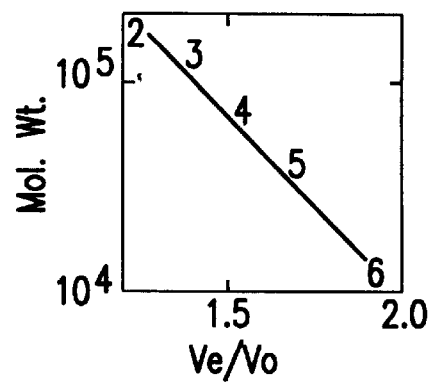

FIG. 3. A graph showing the gel filtration of rHib porin. Inclusion bodies were extracted with 6 M guanidine HCl, and detergent was added as described in Example 6. The mixture was centrifuged to remove any residual material and applied to a 180×2.5 cm S-300 column equilibrated in 100 mM Tris-HCl, 10 mM EDTA, 1 M NaCl, 0.05% 3,14-zwittergent, pH=8.0. A second batch was then applied in the same buffer plus 20 mM $CaCl_2$. The optical density at 280 nm was measured for each fraction. The arrows indicate the elution position of molecular weight markers (Sigma); 1=blue dextran (2,000,000 daltons), 2=alcohol dehydrogenase (150,000 daltons); 4=bovine serum albumin; and 6=cytochrome C (12,400 daltons). The insert shows a semi-log plot of apparent molecular weight versus the elution position. Number 3 is the position of the major peak of the calcium ion treated porin, while number 5 is the position of the major peak of the untreated porin.

FIG. 4. The DNA sequence of the SalI-SalI fragment of pNV-1. Restriction sites are underlined. The synthetic oligonucleotides used to sequence the DNA are shown doubly underlined. The arrows indicate the direction of the squencing reaction. Those with left-arrows are complementary to the shown sequence. The rest of the plasmid is identical to pUC18. The lac promotor is adjacent to the lower SalI site.

FIG. 5. The DNA sequence of the BamHI-XhoI fragment of pNV-2. The portion of the pET-17b vector that encodes the fusion sequence is shown in bold. Restriction sites are underlined. The rest of the plasmid is identical to pET-17b.

FIG. 6. The DNA sequence of the NdeI-XhoI fragment of pNV-3. Restriction sites are underlined. The rest of the plasmid is identical to pET-17b.

FIG. 7. The DNA sequence of the NdeI-BamHI fragment of pNV-6. Restriction sites are underlined. The rest of the plasmid is identical to pET-11a.

DETAILED DESCRIPTION OF THE INVENTION

The present invention relates to a method of expressing the outer membrane protein P2 from *Haemophilus influenzae* type b or a fusion protein thereof.

In one embodiment, the present invention relates to a method of expressing the outer membrane protein P2 from *Haemophilus influenzae* type b or fusion protein in *E. coli* comprising:

(a) transforming *E. coli* by a vector comprising a selectable marker and a gene coding for a protein selected from the group consisting of (i) a mature P2 protein, and (ii) a fusion protein comprising a mature P2 protein fused to amino acids 1 to 22 of the T7 gene φ10 capsid protein;

wherein said gene is operably linked to the T7 promoter; and (b) growing the transformed *E. coli* in LB media containing glucose and a selection agent to which *E. coli* is sensitive (preferably, carbenicillin) at about 30° C.; whereby the Hib-P2 or fusion protein thereof is expressed, wherein the Hib-P2 protein or fusion protein thereof so expressed comprises more than about 2% of the total protein expressed in the *E. coli*. In a preferred embodiment, the Hib-P2 protein or fusion protein so expressed comprises more than about 5% of the total protein expressed in *E. coli*. In another preferred embodiment, the Hib-P2 protein or fusion protein so expressed comprises more than about 10% of the total protein expressed in *E. coli*. In yet another preferred embodiment, the Hib-P2 protein or fusion protein so expressed comprises more than about 40% of the total protein expressed in *E. coli*.

In another preferred embodiment, the vector comprises a Hib-P2 gene operably linked to the T7 promoter of expression plasmids pET-17b, pET-11a, pET-24a–d(+) or pET-9a, all of which are commercially available from Novagen (565 Science Drive, Madison, Wis. 53711). Plasmids pET-17b, pET-9a and pET-24a–d(+) comprise, in sequence, a T7 promoter, a ribosome binding site, restriction sites to allow insertion of the structural gene and a T7 terminator sequence. In addition, plasmid pET11a has a lac operator fused to the T7 promotor and a copy of the lacI gene. The plasmid constructions employed in the present invention are different than those used in Munson, Jr., R. and Tolan, Jr., R. W., *Infection and Immunity* 57:88–94 (January 1989) and allow for an unexpectedly high production of the P2 proteins and fusion proteins.

The transformed *E. coli* are grown in a medium containing a selection agent, e.g. any β-lactam to which *E. coli* is sensitive such as carbenicillin. The pET expression vectors provide selectable markers which confer antibiotic resistance to the transformed organism.

According to the present invention, an extraneous 3' portion down stream from the P2 gene containing P2 termination sequences is eliminated. The fragment thus constructed ends about 40 bp after the translational stop codon.

Any *E. coli* strain encoding T7 polymerases may be used in the practice of the invention. In a preferred embodiment, *E. coli* strain BL21 (DE3) ΔompA is employed. The above mentioned plasmids may be transformed into this strain or the wild-type strain BL21(DE3). The strain BL21 (DE3) ΔompA is a lysogen of bacteriophage λ DE3, which contains the T7 RNA polymerase gene under the control of the inducible lacUV5 promoter. *E. coli* strain BL21 (DE3) ΔompA is preferred as no OmpA protein is produced by this strain which might contaminate the purified porin protein and create undesirable immunogenic side effects. The transformed *E. coli* of the present invention may be grown in LB broth containing glucose and carbenicillin and grown and induced at about 30° C. and at a low aeration rate (about 150 rpm). Under these conditions, a high level of P2 expression was obtained.

Long term, high level expression of P2 can be toxic in *E. coli*. The highest expression level of Hib-P2 which has been reported is less than 2% of the total proteins expressed (Munson, Jr., R. and Tolan, Jr., R. W., *Infection and Immunity* 57(1):88–94 (January 1989)). Surprisingly, the present invention allows *E. coli* to express the Hib-P2 protein and fusion protein thereof to a level of about 35–50%, as measured by densitometry on an electrophoresis gel after staining with Coomassie blue.

In another preferred embodiment, the present invention relates to a vaccine comprising the outer membrane protein P2 from *Haemophilus influenzae* type b (Hib-P2) or fusion protein thereof, produced according to the above-described methods, together with a pharmaceutically acceptable diluent, carrier, or excipient, wherein the vaccine may be administered in an amount effective to elicit protective antibodies in an animal to *Haemophilus influenzae* type b. In a preferred embodiment, the animal is selected from the group consisting of humans, cattle, pigs, sheep, and chickens. In another preferred embodiment, the animal is a human.

In another preferred embodiment, the present invention relates to the above-described vaccine, wherein said outer membrane protein P2 or fusion protein thereof is conjugated to a Haemophilus capsular polysaccharide (CP). Haemophilus CPs may be prepared or synthesized as described in Schneerson et al. *J. Exp. Med.* 152:361–376 (1980); Marburg et al. *J. Am. Chem. Soc.* 108:5282 (1986); Jennings et al., *J. Immunol.* 127:1011–1018 (1981); and Beuvery et al., *Infect. Immunol.* 40:39–45 (1983); the contents of each of which are fully incorporated by reference herein.

In a further preferred embodiment, the present invention relates to a method of preparing a polysaccharide conjugate comprising: obtaining the above-described outer membrane protein P2 or fusion protein; obtaining a CP or fragment from a Haemophilus organism; and conjugating the outer membrane protein P2 or fusion protein to the CP or CP fragment.

The conjugates of the invention may be formed by reacting the reducing end groups of the CP fragment to primary amino groups of the porin by reductive amination. The reducing groups may be formed by selective hydrolysis or specific oxidative cleavage, or a combination of both. Preferably, the CP is conjugated to the porin protein by the method of Jennings et al., U.S. Pat. No. 4,356,170, the contents of which are fully incorporated by reference herein, which involves controlled oxidation of the CP with periodate followed by reductive amination with the porin protein.

The vaccine of the invention comprises the Hib-P2 protein, fusion protein or conjugate vaccine in an amount effective depending on the route of administration. Although subcutaneous or intramuscular routes of administration are preferred, the Hib-P2, fusion protein or vaccine of the present invention can also be administered by an intraperitoneal or intravenous route. One skilled in the art will appreciate that the amounts to be administered for any particular treatment protocol can be readily determined without undue experimentation. Suitable amounts might be expected to fall within the range of 2 micrograms of the protein per kg body weight to 100 micrograms per kg body weight.

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the Hib-P2 protein, fusion protein or conjugate vaccine have suitable solubility properties. The vaccines may be in the form of single dose preparations or in multi-dose flasks which can be used for mass vaccination programs. Reference is made to Remington's *Pharmaceutical Sciences*, Mack Publishing Co., Easton, Pa., Osol (ed.) (1980); and *New Trends and Developments in Vaccines*, Voller et al. (eds.), University Park Press, Baltimore, Md. (1978), for methods of preparing and using vaccines.

The Hib-P2 protein or conjugate vaccines of the present invention may further comprise adjuvants which enhance production of P2 antibodies. Such adjuvants include, but are not limited to, various oil formulations such as Freund's complete adjuvant (CFA), the dipeptide known as MDP, saponin, aluminum hydroxide, or lymphatic cytokine.

Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Hib-P2 protein, fusion protein or a conjugate vaccine thereof may be absorbed onto the aluminum hydroxide from which it is slowly released after injection. Hib-P2 protein, fusion protein or conjugate vaccine may also be encapsulated within liposomes according to Fullerton, U.S. Pat. No. 4,235,877.

In another preferred embodiment, the present invention relates to a method of preventing bacterial meningitis in an animal comprising administering to the animal the Hib-P2 protein or conjugate vaccine produced according to methods described in an amount effective to prevent bacterial meningitis.

In a further embodiment, the invention relates to a method of purifying the above-described outer membrane protein P2 or fusion protein, comprising: lysing the transformed *E. coli* to release the P2 protein or fusion protein as part of insoluble inclusion bodies; washing the inclusion bodies with a buffer to remove contaminating *E. coli* cellular proteins; resuspending and dissolving the inclusion bodies in an aqueous solution of a denaturant; diluting the resultant solution in a detergent; and purifying the solubilized P2 protein or fusion protein by gel filtration in the absence of denaturant.

The lysing step may be carried out according to any method known to those of ordinary skill in the art, e.g. by sonication, enzyme digestion, osmotic shock, or by passing through a mull press.

The inclusion bodies may be washed with any buffer which is capable of solubilizing the *E. coli* cellular proteins without solubilizing the inclusion bodies comprising the P2 protein or fusion protein. Such buffers include but are not limited to TEN buffer (50 mM Tris HCl, 1 mM EDTA, 100 mM NaCl, pH 8.0). Other buffers can be used such as Bicine, Tricine and HEPES.

Denaturants which may be used in the practice of the invention include 2 to 8 M urea or about 2 to 6 M guanidine HCl, more preferably, 4 to 8 M urea or about 4 to 6 M guanidine HCl, and most preferably, about 8 M urea or about 6 M guanidine HCl.

Examples of detergents which can be used to dilute the solubilized P2 protein or fusion protein include, but are not limited to, ionic detergents such as SDS and CETAVLON (Aldrich); non-ionic detergents such as TWEEN, TRITON X-100, and octyl glucoside; and zwitterionic detergents such as 3,14-ZWITTERGENT, and Chaps.

Finally, the solubilized P2 protein or fusion protein may be purified by gel filtration to separate the high and low molecular weight materials. Types of filtration gels include but are not limited to SEPHACRYL (bead-formed ally dextron-N,N'-methylene bisacrylamide gel matrix)300, SEPHAROSE (bead-formed agarose gel matrix) CL-6B, and BIO-GEL (bead-formed agarose gel matrix) A-1.5$\mu$. The column is eluted with the buffer used to dilute the solubilized protein. The fractions containing the P2 protein or fusion thereof may then be identified by gel electrophoresis, the fractions pooled, dialyzed, and concentrated.

Finally, substantially pure (>95%) P2 protein and fusion protein may be obtained by passing the concentrated fractions through a FAST FLOW Q SEPHAROSE(bead-formed agarose gel matrix) HIGH PERFORMANCE COLUMN (Pharmacia).

In another embodiment, the present invention relates to expression of Hib-P2 in a yeast Pichia expression system (Sreekrishna et al., *J. Basic Microbiol.* 28:265–278 (1988)), and an archaebacteria expression system (Blaseio and Pfeifer, *Proc. Natl. Acad. Sci. U.S.A.* 87:6772–6776 (1990); Cline et al., *J. Bacteriol.* 171:4987–4991 (1989)). The cloning of the P2 protein gene or fusion gene into an expression vector may be carried out in accordance with conventional techniques, including blunt-ended or staggerended termini for ligation, restriction enzyme digestion to provide appropriate termini, filling in of cohesive ends as appropriate, alkaline phosphatase treatment to avoid undesirable joining, and ligation with appropriate ligases. Reference is made to Sambrook et al., *Molecular Cloning: A Laboratory Manual*, 2nd ed., Cold Spring Harbor, N.Y., Cold Spring Harbor Laboratory Press (1989), for general methods of cloning.

The Hib-P2 and fusion protein expressed according to the present invention must be properly refolded in order to achieve a structure which is immunologically characteristic of the native protein. In yet another embodiment, the present invention relates to a method of refolding the above-described outer membrane protein P2 or fusion protein, comprising: lysing the transformed *E. coli* to release the outer membrane protein P2 or fusion protein as part of insoluble inclusion bodies; washing the inclusion bodies with a buffer to remove contaminating *E. coli* cellular proteins; resuspending and dissolving the inclusion bodies in an aqueous solution of a denaturant; resuspending and dissolving the outer membrane protein P2 in high salt (preferably, 2 to 8 M urea or about 2 to 6 M guanidine HCl, more preferably, 4 to 8 M urea or about 4 to 6 M guanidine HCl, and most preferably, about 8 M urea or about 6 M guanidine HCl); diluting the resultant solution in a detergent (preferably, zwittergent, SDS, or TWEEN-20); and purifying the outer membrane protein P2 by gel filtration; and storing the gel filtration product at about 1° C. to about 15° C. (preferably, about 4° C.) until the outer membrane protein P2 refolds (preferably, one to 10 weeks; most preferably, about three weeks).

The gel filtration step separates high and low molecular weight material and allows the separation of trimeric and monomeric porin.

After the gel filtration step, high levels of salt (1 to 4M NaCl) are required initially to keep the porin in solution. Calcium ions (preferably, 1 mM to 1M $CaCl_2$; most preferably, about 20 mM $CaCl_2$), but not magnesium or manganese ions, are required for efficient aggregation of the rHib porin. At this stage, while the rHib porin is trimeric, the conformation is not "native" because when the salt is removed, the porin precipitates from solution. This does not occur with wild-type Hib porin. However, as the porin is stored at 4° C., a slow conformational change occurs which allows the salt to be removed without precipitation of the porin.

The protein at this stage is about 80 to 90 percent pure as judged by coomassie blue stained SDS-PAGE. This material is then applied to an ion exchange column and eluted with a salt gradient. The resulting material is ~95% pure.

In another preferred embodiment, the present invention relates to a substantially pure refolded outer membrane protein P2 from *Haemophilus influenzae* type b (Hib-P2) produced according to the above-described methods. A substantially pure protein is a protein that is generally lacking in other cellular *Haemophilus influenzae* components as evidenced by, for example, electrophoresis. Such substantially pure proteins have a purity of >95%, as measured by densitometry on an electrophoretic gel.

The present invention is described in further detail in the following non-limiting examples.

EXAMPLE 1

Cloning of the Outer Membrane Protein P2 from *Haemophilus Influenzae* Type B

Total genomic DNA was isolated from 0.5 g of *Haemophilus influenzae* type b strain Eagan using methods previously described (Sambrook et al., *Molecular Cloning: A Laboratory Manual*, 2nd ed., Cold Spring Harbor, N.Y., Cold Spring Harbor Laboratory Press (1989)). This DNA was then used as a template for two P2 specific oligonucleotides in a polymerase chain reaction (PCR) using standard PCR conditions (U.S. Pat. No. 4,683,195; U.S. Pat. No. 4,683,202; Saiki et al., *Science* 230:1350–1354 (1985); Innis et al., *PCR Protocols: A Guide to Methods and Applications*, Academic Press, Inc., San Diego, Calif. (1990), the contents of which are fully incorporated by reference herein).

The 5' P2 specific oligonucleotide was designed to be 40 bp 5' of the ATG (start codon) and had the sequence (SEQ ID NO:1):

5' TTC-TGG-CGA-GTC-GAC-AAT-TCT-ATT-GG 3'.

The 3' P2 specific oligonucleotide was designed to be 300 bp 3' of the stop codon and had the sequence (SEQ ID NO:2):

5' AAC-CTT-TAT-CGT-CGA-CGA-GCA-ATT-GG 3'.

Both of the P2 specific oligonucleotides contained SalI restriction enzyme sites to facilitate cloning of the amplified product.

Subsequent to the PCR amplification reaction, the amplified DNA was isolated by electrophoresis on a 0.8% agarose gel. The gel demonstrated a single 1.4 kb band. This DNA was purified from the gel and digested with three restriction enzymes (EcoRI, DraI, PvuII) that yielded bands of predictable sizes. The 1.4 kb fragment was then digested with SalI and ligated to SalI digested pUC18 (Yanisch-Perron et al. *Gene* 33:103–119) using T4 DNA ligase.

The ligation mixture was used to transform competent *E. coli* strain DH5α (Sambrook et al., *Molecular Cloning: A Laboratory Manual*, 2nd ed., Cold Spring Harbor Laboratory Press, Cold Spring Harbor, N.Y. (1989)). Resulting colonies were isolated and then analyzed by preparing mini-prep DNAs. The DNAs were analyzed by digesting with SalI which yielded a vector band of 2.7 kb and a fragment band of 1.4 kb.

The ligation that generated plasmid pNV-1 was nondirectional. This means that the DNA insert should be present in both orientations. To test the orientation of the insert, the plasmid was digested with both MluI and NarI. The size of the resulting fragments indicates whether the insert is oriented in the same direction as the lac promotor, or in the opposite direction. Several isolates of the plasmid were tested and all were found to be in the opposite direction to the lac promotor. Evidently, the inserts that were in the same direction as the promotor were selected against during growth. This suggests that expression of the rHib P2 is toxic in *E. coli*. Similar conclusions were reached earlier by Munson's group (Munson and Tolan, *Infect. Immunity* 57:88–94 (1989)) and by Hansen's group (Hansen et al., *Infect. Immunity* 56:2709–2716 (1989)).

Clones containing the 1.4 kb fragment were chosen for DNA sequence analysis. One clone designated pNV-1 was sequenced in both directions using the Sanger method (Sanger et al., *Proc. Natl. Acad. Sci. USA* 74:5463 (1977)). pNV-1 was found to be identical to the published sequence for Hib strain Minn A (Munson, Jr., R. and Tolan, Jr., R. W., *Infection and Immunity* 57:88σ(January 1989)).

Molecular biological techniques used herein may be found in Sambrook et al., *Molecular Cloning: A Laboratory Manual*, 2nd ed., Cold Spring Harbor, N.Y., Cold Spring Harbor Laboratory Press (1989) and Ausubel et al., *Current Protocols in Molecular Biology*, Vols. 1 and 2, Wiley-Liss, New York, N.Y. (1992), the contents of which are fully incorporated by reference herein.

EXAMPLE 2

Construction of Expression Vectors Containing the Outer Membrane Protein P2 Gene The expression vector, pET-17b (Novagen pET System Manual), was used for the expression of P2. This plasmid utilizes the phage T7 φ10 gene promotor. This promotor is not recognized by *E. coli* DNA dependent RNA polymerase, and thus will not produce substantial levels of the porin unless T7 RNA polymerase is present. Strain BL21 (DE3) contains a lysogenic λ phage that encodes the required polymerase under control of the lacUV5 promotor. Two types of recombinant P2 proteins were made using the pET-17b expression vector. One type was the mature P2 containing a methionine at the N-terminus. The second type was a fusion protein (designated fusion-P2) containing the mature P2 with 22 amino acids of gene 10 of phage T7 at the N-terminus that were derived from the pET-17b vector.

To clone the P2 into pET-17b, the original P2 gene (in pNV-1) was modified using PCR. To construct the mature-P2, an oligonucleotide was constructed that allowed the mature porin to be cloned into the NdeI site of pET 17b, thus producing the mature-P2. The oligonucleotide designed for this had the sequence (SEQ ID NO:3):

5' GCT-TCA-GCA-GCA-CAT-ATG-GCT-GTT-GTT-TAT-AAC-AAC-GAA-GGG-AC-3'.

To construct the fusion-P2, an oligonucleotide was constructed that allowed the mature porin to be cloned into the BamHI site of pET 17b, thus yielding a fusion P2 to gene 10 which is a major capsid protein of T7. The sequence (SEQ ID NO:4) of this oligonucleotide was:

5' GCA-GCT-TCA-GCA-GCG-GAT-CCA-GCT-GTT-GTT-TAT-AAC-AAC-GAA-GGG-3'.

The extraneous 3' sequences were eliminated by introducing a xhoI site about 40 bp from the translational stop codon. This oligonucleotide was designed to contain an XhoI site to allow it to be cloned into the XhoI site of pET-17b. The sequence (SEQ ID NO:5) of this oligonucleotide was:

5'GC-AAA-AAA-AGC-GAA-TCT-CTC-GAG-TCG-CCT-TGC-TTT 3'.

PCR was used to generate a 1.1 kb fragment from the full length P2 (pNV-1) with the 5' oligonucleotide containing the NdeI site and the 3' oligonucleotide containing the XhoI site. This fragment was digested with NdeI and XhoI, purified and ligated into NdeI-XhoI digested pET 17b. This resulted in the mature-P2 construct (pNV-3 or N-X).

Likewise, a 1.1 kb fragment was generated from the full length pNV-1 with the 5' oligonucleotide containing the BamHI site and the 3' oligonucleotide containing the XhoI site using PCR. This fragment was digested with BamHI and XhoI purified and ligated into the BamHI-XhoI digested pET-17b. This yielded the fusion-P2 construct (pNV-2 or B-X). Both of the constructs were transformed into *E. coli* DH5α strain which lacks T7 polymerase. Plasmid DNA was isolated from numerous DH5α transfonnants. Both the mature-P2 and fusion-P2 constructs were sequenced at their 5' and 3' end to ensure that the cloning junctions were correct.

FIG. 1 shows the kinetics of induction by IPTG of *E. coli* strain BL21 (DE3) [pNV-3]. Note that even before addition of the gratuitous inducer, there are significant levels of the porin present. This is because the lacUV5 promotor is not fully repressed. The level of porin rapidly increases and reaches a maximum after about three hours.

Porin expression in strain BL21 (DE3) is still toxic. This is due to the significant uninduced levels of the porin observed in FIG. 1. Care must be taken in handling this strain (keep frozen when not in use; induce at 30° C.) because deletions or other mutations will be selected that do not produce porin.

EXAMPLE 3

Construction of pNV-6

Plasmid pET-11a (Novagen pET System Manual) has the same expression signals as pET-17b. However, this plasmid also contains the lac operator adjacent to the T7 gene φ10 promotor. This places the T7 promotor under regulation of the lac repressor. pET-11a also encodes an extra copy of the lacI gene that encodes the lac repressor. This construction should result in substantially lower uninduced levels of porin.

Plasmid pET-11a contains fewer usable restriction sites than pET17b. There is a NdeI site in the same location as in pET17b thus allowing reuse of oligonucleotide SEQ IN NO:3 at the 5' end of the P2 gene. However, there is no XhoI site available. Instead, a BamHI site is incorporated using the oligonucleotide (SEQ ID NO:6):

AAA-AAA-AGC-GAA-TCT-TTG-GAT-CCG-CCT-TGC-TTT-TAA-TAA-TG

PCR was used to generate a new 1.1 kb fragment from full length P2 (pNV-1) with the oligonucleotides 3 and 6. This fragment was digested with NdeI and BamHI, purified and ligated into pET11a previously cut with NdeI-BamHI. This resulted in a second mature-P2 construct (pNV-6). Both the 5' and the 3' ends of this construction were sequenced to ensure the cloning junctions were correct. pNV6 was deposited on Jul. 17, 1998, in DH5α *E. coli* cells, at the American Type Culture Collection, 10801 University Blvd., Manassas, Va., under accession no. 98819.

FIG. 2 shows the kinetics of induction of BL21 (DE3) [pNV-6]. Notice that the uninduced levels of the porin are much lower than observed with plasmid pNV-3. The time required to reach the maximum level of induction is slightly longer than observed with pNV-3 but after three hours, the levels of porin are comparable with pNV-3. The lower uninduced levels of porin observed in pNV-6 means that this plasmid should show lower levels of toxicity than plasmid pNV-3 and thus should be more stable.

EXAMPLE 4

Construction of Expression Strain BL21 (DE3) ΔompA

*Escherichia coli* strains DME558 (from the collection of S. Benson; Silhavy, T. J. et al., "Experiments with Gene Fusions," Cold Spring Harbor Laboratory, Cold Spring Harbor, N.Y., 1984), BRE51 (Bremer, E. et al., *FEMS Microbiol. Lett.* 33:173–178 (1986)) and BL21 (DE3) were grown on LB agar plates at 37° C.

P1 Transduction: A P1$_{vir}$ lysate of *E. coli* strain DME558 was used to transduce a tetracycline resistance marker to strain BRE51 (Bremer, E., et al., *FEMS Microbiol. Lett.* 33:173–178 (1986)) in which the entire ompA gene had been deleted (Silhavy, T. J., et al., *Experiments with Gene Fusions*, Cold Spring Harbor Laboratory, Cold Spring Harbor, N.Y. (1984)). Strain DME558, containing the tetracycline resistance marker in close proximity of the ompA gene, was grown in LB medium until it reached a density of approximately 0.6 OD at 600 nm. One tenth of a milliliter of 0.5 M CaCl$_2$ was added to the 10 ml culture and 0.1 ml of a solution containing 1×10$^9$ PFU of P1$_{vir}$. The culture was incubated for 3 hours at 37° C. After this time, the bacterial cell density was visibly reduced. 0.5 ml of chloroform was added and the phage culture stored at 4° C. Because typically 1–2% of the *E. coli* chromosome can be packaged in each phage, the number of phage generated covers the entire bacterial host chromosome, including the tetracycline resistance marker close to the ompA gene.

Next, strain BRE51, which lacks the ompA gene, was grown in LB medium overnight at 37° C. The overnight culture was diluted 1:50 into fresh LB and grown for 2 hr. The cells were removed by centrifugation and resuspended in MC salts. 0.1 ml of the bacterial cells were mixed with 0.05 of the phage lysate described above and incubated for 20 min. at room temperature. Thereafter, an equal volume of 1 M sodium citrate was added and the bacterial cells were plated out onto LB plates containing 12.5 μg/ml of tetracycline. The plates were incubated overnight at 37° C. Tetracycline resistant (12 μg/ml) transductants were screened for lack of OmpA protein expression by SDS-PAGE and Western Blot analysis, as described below. The bacteria resistant to the antibiotic have the tetracycline resistance gene integrated into the chromosome very near where the ompA gene had been deleted from this strain. One particular strain was designated BRE-T$^R$.

A second round of phage production was then carried out with the strain BRE-T$^R$, using the same method as described above. Representatives of this phage population contain both the tetracycline resistance gene and the ompA deletion. These phage were then collected and stored. These phage were then used to infect *E. coli* BL21(DE3). After infection, the bacteria contained the tetracycline resistance marker. In addition, there is a high probability that the ompA deletion was selected on the LB plates containing tetracycline.

Colonies of bacteria which grew on the plates were grown up separately in LB medium and tested for the presence of the OmpA protein. Of those colonies selected for examination, all lacked the OmpA protein as judged by antibody reactivity on SDS-PAGE western blots.

The SDS-PAGE was a variation of Laenunli's method (Laemmli, U. K., *Nature* 227:680–685 (1970)) as described previously (Blake and Gotschlich, *J. Exp. Med.* 159:452–462 (1984)). Electrophoretic transfer to Immobilon P (Millipore Corp. Bedford, Mass.) was performed according to the methods of Towbin et al. (Towbin, H., et al., *Proc. Natl. Acad. Sci. USA* 76:4350–4354 (1979)) with the exception that the paper was first wetted in methanol. The Western blots were probed with phosphatase conjugated reagents (Blake, M. S., et al., *Analyt. Biochem.* 136:175–179 (1984)).

EXAMPLE 5

Expression of the Outer Membrane Protein P2

The mature-P2 and Fusion-P2 constructs were used to transform the expression strain BL21 (DE3) ΔompA. The transformation plates were cultured at 30° C. Colonies of both types were isolated from these plates and analyzed. It was found that virtually all transformants contained the desired plasmid DNA.

Various fusion-P2 and mature-P2 containing clones were then analyzed for protein expression. The clones were induced and grown in LB media containing 0.4% glucose and 118 μM carbenicillin instead of ampicillin with an aeration speed of 100 to 150 rpm and at about 30° C. The expression of the P2 protein was analyzed by loading 0.1 ml of the culture of total *E. coli* proteins on an 8–16% gradient SDS gel (see FIGS. 1 and 2).

EXAMPLE 6

Purification and Refolding of the Outer Membrane Protein P2

*E. coli* strain BL21 (DE3) ΔompA [pNV-3] is grown to mid-log phase (OD=0.6 at 600 nm) in Luria broth. Isopropyl thiogalactoside is then added (0.4 mM final) and the cells grown an additional three hours at 30° C. The cells were then harvested and washed with several volumes of TEN buffer (50 mM Tris-HCl, 0.2 M NaCl, 10 mM EDTA, pH=8.0) and the cell paste stored frozen at −75° C.

For purification about 3 grams of cells are thawed and suspended in 9 ml of TEN buffer. Lysozyme is added (Sigma, 0.25 mg/ml) deoxycholate (Sigma, 1.3 mg/ml) plus PMSF (Sigma, 10 μg/ml) and the mixture gently shaken for one hour at room temperature. During this time, the cells lyse and the released DNA causes the solution to become very viscous. DNase is then added (Sigma, 2 μg/ml) and the solution again mixed for one hour at room temperature. The mixture is then centrifuged at 15 K rpm in an SA-600 rotor for 30 minutes and the supernatant discarded. The pellet is then twice suspended in 10 ml of TEN buffer and the supernatants discarded. The pellet is then suspended in 10 ml of 8 M urea (Pierce) in TEN buffer. Alternatively, the pellet is suspended in 10 ml of 6 M guanidine HCl (Sigma) in TEN buffer. The mixture is gently stirred to break up any clumps. The suspension is sonicated for 20 minutes or until an even suspension is achieved. 10 ml of a 10% aqueous solution of 3,14-ZWITTERGENT is added and the solution thoroughly mixed. The solution is again sonicated for 10 minutes. Any residual insoluble material is removed by centrifugation.

This mixture is then applied to a 180×2.5 cm column of Sephacryl-300 (Pharmacia) equilibrated in 100 mM Tris-HCl, 1 M NaCl, 10 mM EDTA, 20 mM CaCl$_2$, 0.05% 3,14-ZWITTERGENT, pH=8.0. The flow rate is maintained at 1 ml/min. Fractions of 10 ml are collected. The porin refolds into trimer during the gel filtration. The OD=280 nm of each fraction is measured and those fractions containing protein are subjected to SDS gel electrophoresis assay for porin. Those fractions containing porin are pooled and stored at 4° C. for three weeks. During the incubation at 4° C., a slow conformational change occurs. This is necessary for the protein to remain in solution without the elevated levels of salt. The pooled fractions are then dialyzed against 50 mM Tris-HCl, 200 mM NaCl, 10 mM EDTA, 0.05% 3,14-ZWITTERGENT, pH=8.0. This material is then applied to a 2.5× cm Fast Flow Q (Phannacia) column equilibrated in the same buffer. Any unbound protein is then eluted with starting buffer. A linear 0.2 to 2.0 M NaCl gradient is then applied to the column. The porin elutes just before the center of the gradient. Fractions are assayed by SDS-PAGE and the purest fractions pooled and dialyzed against TEN buffer containing 0.05% 3,14-ZWITTERGENT.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method for the high level expression of an outer membrane protein P2 from *Haemophilus influenzae* type b (Hib-P2) in *E. coli* comprising:
   (a) transforming *E. coli* host cells with a vector comprising a selectable marker and a gene coding for a P2 protein selected from the group consisting of
      (i) a mature P2 protein, and
      (ii) a fusion protein comprising a mature P2 protein fused to amino acids 1 to 22 of the T7 gene φ10 capsid protein (SEQ. ID NO: 10);
      wherein said gene is operably linked to a T7 promoter; and
   (b) growing said transformed *E. coli* in media containing glucose and a selection agent at about 30° C.; whereby said P2 protein is expressed and is found in inclusion bodies, wherein said P2 protein comprises more than about 2% of the total protein expressed in said *E. coli*.

2. The method according to claim 1, wherein the P2 protein expressed comprises more than about 10% of the total protein expressed in said *E. coli*.

3. The method according to claim 1, wherein said P2 protein expressed comprises more than about 40% of the total protein expressed in said *E. coli*.

4. The method according to claim 1, wherein said vector is selected from the group consisting of pET-17b, pET-11a, pET-24a–d(+) and pET-9a.

5. The method according to claim 1, wherein said vector comprises a Hib-P2 gene operably linked to the T7 promoter of expression plasmid pET-17b.

6. The vector pNV-3.

7. The vector pNV-2.

8. The vector pNV-6.

9. The method of claim 1, wherein said gene codes for a fusion protein comprising a mature P2 protein fused to amino acids 1 to 22 of the T7 gene φ10 capsid protein (SEQ. ID NO: 10).

10. The method of claim 1, wherein said gene codes for a mature P2 protein.

11. The method of claim 1, wherein said media is Luria Broth media.

12. A method for purifying and refolding recombinantly produced *Haemophilus influenzae* type b outer membrane P2 protein, wherein said P2 protein is selected from the group consisting of
(i) a mature P2 protein, and
(ii) a fusion protein comprising a mature P2 protein fused to amino acids 1 to 22 of the T7 gene φ10 capsid protein (SEQ. ID NO: 10), the method comprising:
(a) lysing *E. coli* host cells capable of expressing said P2 protein to release the P2 protein as insoluble inclusion bodies;
(b) washing said insoluble inclusion bodies with a buffer to remove contaminating *E. coli* cellular proteins;
(c) suspending and dissolving the inclusion bodies obtained in step (b) in an aqueous solution of a denaturant;
(d) diluting the suspended and dissolved inclusion bodies obtained in step (c) with a zwitterionic detergent to give a zwitterionic detergent containing solution;
purifying said P2 protein in said zwitterionic detergent containing solution further comprising a sufficient amount of NaCl and $CaCl_2$, so that a partially refolded, trimeric P2 protein is obtained; and
(f) storing said partially refolded, trimeric P2 protein obtained in step (e) in an aqueous solution for a sufficient amount of time to achieve a fully refolded P2 protein.

13. The method of claim 12, wherein in step (e), said zwitterionic detergent containing solution contains about 1M to 4M NaCl and about 1 mM to 1M $CaCl_2$.

14. The method of claim 13, wherein in step (e), said zwitterionic detergent solution contains about 1M NaCl and about 20 mM $CaCl_2$.

15. The method of claim 12, wherein in step (f), said protein is stored at temperature of about 1–15° C.

16. The method of claim 15, wherein in step (f), said protein is stored at a temperature of about 4° C.

17. The method of claim 12, wherein in step (f), said protein is stored for about 1–10 weeks.

18. The method of claim 17, wherein in step (f), said protein is stored for about 3 weeks.

19. The method according to claim 12, wherein said P2 protein comprises a mature P2 protein.

20. The method of claim 12, wherein said P2 protein comprises a fusion protein comprising a mature P2 protein fused to amino acids 1 to 22 of the T7 gene φ10 capsid protein (SEQ. ID NO: 10).

21. A method of obtaining a conjugate of a purified and refolded recombinantly produced *Haemophilus influenzae* type b outer membrane P2 protein and a polysaccharide, wherein said P2 protein is selected from the group consisting of
(i) a mature P2 protein, and
(ii) a fusion protein comprising a mature P2 protein fused to amino acids 1 to 22 of the T7 gene φ10 capsid protein (SEQ. ID NO: 10), the method comprising:
(a) lysing *E. coli* host cells capable of expressing said P2 protein to release the P2 protein as insoluble inclusion bodies;
(b) washing said insoluble inclusion bodies with a buffer to remove contaminating *E. coli* cellular proteins;
(c) suspending and dissolving the inclusion bodies obtained in step (b) in an aqueous solution of a denaturant;
(d) diluting said suspended and dissolved inclusion bodies obtained in step (c) with a zwitterionic detergent to give a zwitterionic detergent containing solution;
(e) purifying said P2 protein in said zwitterionic detergent containing solution further comprising a sufficient amount of NaCl and $CaCl_2$, so that a partially refolded, trimeric P2 protein is obtained;
(f) storing said partially refolded, trimeric P2 protein obtained in step (e) in an aqueous solution for a sufficient amount of time to achieve a fully refolded P2 protein;
(g) obtaining a Haemophilus capsular polysaccharide; and
(h) conjugating the fully refolded P2 protein obtained in step (f) to the polysaccharide of (g).

22. The method according to claim 21, wherein said P2 protein comprises a mature P2 protein.

23. The method according to claim 21, wherein said P2 protein comprises a fusion protein comprising a mature P2 protein fused to amino acids 1 to 22 of the T7 gene φ10 capsid protein (SEQ. ID NO: 10).

24. The method of claim 12 or 21, wherein said purifying is by gel filtration.

25. The method of claim 12 or 21, wherein said zwitterionic detergent is 3,14-ZWITTERGENT (n-tetradecyl-N, N-dimethyl-3-ammonio-1-propanesulfonate).

26. A method of obtaining a fully refolded Hib-P2 porin, comprising storing a partially refolded Hib-P2 porin in the presence of a sufficient amount of a zwitterionic detergent, NaCl and $CaCl_2$ for a time sufficient to obtain the fully refolded porin.

27. The method of claim 26, wherein said zwitterionic detergent is 3,14-ZWITTERGENT (n-tetradecyl-N,N-dimethyl-3-ammonio-1-propanesulfonate).

28. A trimeric, fully refolded porin comprising a fusion protein comprising a mature outer membrane protein P2 from *Haemophilus influenzae* type b (Hib-P2) covalently linked to a N-terminal fragment, including the leader sequence, of the T7 gene φ10 capsid protein (SEQ ID NO: 10).

29. The trimeric, fully refolded porin of claim 28, wherein said mature outer membrane protein P2 is covalently linked to amino acids 1 to 22 of the T7 gene φ10 capsid protein.

30. A vaccine comprising an immunologically effective amount of said porin of claim 28 together with a pharmaceutically acceptable diluent, carrier or excipient.

31. The vaccine of claim 30, wherein said fusion protein is conjugated to a capsular polysaccharide.

32. The vaccine of claim 31, wherein said polysaccharide is from *Haemophilus influenzae*.

33. A method for vaccinating an animal comprising administering to the animal an immunologically effective amount of a recombinantly produced trimeric refolded mature outer membrane protein P2 from *Haemophilus influenzae* type b (Hib-P2), wherein said recombinantly produced trimeric refolded Hib-P2 is obtained by a process comprising:

(a) lysing *E. coli* host cells capable of expressing said mature P2 protein to release said mature P2 protein in the form of inclusion bodies, (b) washing said inclusion bodies with a buffer to remove contaminating *E. coli* cellular proteins, (c) suspending and dissolving the inclusion bodies obtained in step (b) in an aqueous solution of a denaturant, (d) diluting the suspended and dissolved inclusion bodies obtained in step (c) with a zwitterionic detergent to give a zwitterionic detergent containing solution, (e) purifying said suspended and dissolved inclusion bodies in an aqueous solution comprising a zwitterionic detergent and a sufficient amount of NaCl and $CaCl_2$ so that a partially refolded, trimeric P2 protein is obtained, and (f) storing said partially refolded, trimeric P2 protein obtained in step (e) in an aqueous solution for a sufficient amount of time to achieve a fully refolded Hib-P2.

34. The method of claim 33, wherein said refolded mature outer membrane P2 is conjugated to a capsular polysaccharide.

35. The method of claim 34, wherein said capsular polysaccharide is from *Haemophilus influenzae*.

36. A method for vaccinating an animal comprising administering to the animal an immunologically effective amount of the vaccine of claim 30.

37. A method for vaccinating an animal comprising administering to the animal an immunologically effective amount of the vaccine of claim 31.

38. A method for vaccinating an animal comprising administering to the animal an immuniologically effective amount of the vaccine of claim 32.

39. The method of claim 33, wherein in step (e), said purifying is by gel filtration.

40. The porin of claim 28, which is obtained by a process comprising:

(a) lysing *E. coli* host cells capable of expressing said fusion protein to release said fusion protein in the form of insoluble inclusion bodies, (b) washing said insoluble inclusion bodies with a buffer to remove contaminating *E. coli* cellular proteins, (c) suspending and dissolving the insoluble inclusion bodies obtained in step (b) in an aqueous solution of a denaturant, (d) diluting the suspended and dissolved insoluble inclusion bodies obtained in step (c) with a zwitterionic detergent to give a zwitterionic detergent containing solution, (e) purifying said suspended and dissolved insoluble inclusion bodies in an aqueous solution comprising a zwitterionic detergent and a sufficient amount of NaCl and $CaCl_2$ so that a partially refolded, trimeric porin is obtained, and (f) storing said partially refolded, trimeric porin obtained in step (e) in an aqueous solution for a sufficient amount of time to achieve the fully refolded porin.

41. The porin of claim 40, wherein in step (e), said purifying is by gel filtration.

* * * * *